United States Patent [19]

Hansen, Jr. et al.

[11] Patent Number: 5,633,237
[45] Date of Patent: May 27, 1997

[54] IMIDAZO[1,2-A]PYRIDINYLALKYL PHOSPHONIC ACID COMPOUNDS FOR TREATMENT OF NEUROTOXIC INJURY

[75] Inventors: Donald W. Hansen, Jr., Skokie, Ill.; Gilbert W. Adelstein, Morristown, N.J.; Karen B. Peterson, Vernon Hills; Sofya Tsymbalov, Des Plaines, both of Ill.

[73] Assignee: G.D. Searle & Co., Skokie, Ill.

[21] Appl. No.: 271,395

[22] Filed: Jul. 6, 1994

Related U.S. Application Data

[62] Division of Ser. No. 871,995, Dec. 9, 1991, Pat. No. 5,360,796, which is a continuation of Ser. No. 445,228, Dec. 4, 1989, abandoned.

[51] Int. Cl.$^6$ .............. A61K 31/44; C07D 471/04
[52] U.S. Cl. .............. 514/80; 514/212; 514/300; 514/299; 514/301; 514/396; 514/397; 514/398; 514/399; 540/542; 540/597; 546/23; 546/121
[58] Field of Search .............. 514/80, 300, 299, 514/396, 397, 398, 399, 381

[56] References Cited

U.S. PATENT DOCUMENTS

| | | | |
|---|---|---|---|
| 4,450,164 | 5/1984 | Bristol et al. | 424/256 |
| 4,501,745 | 2/1985 | Kaplan et al. | 514/222 |
| 4,588,732 | 5/1986 | Browne | 514/300 |
| 4,650,796 | 3/1987 | George et al. | 514/213 |
| 4,657,899 | 4/1987 | Rzeszotarski et al. | 514/120 |
| 4,746,653 | 5/1988 | Hutchison et al. | 514/89 |

FOREIGN PATENT DOCUMENTS

| | | |
|---|---|---|
| 33094 | 8/1981 | European Pat. Off. . |
| 120589 | 10/1984 | European Pat. Off. . |
| 0 290 003 | 11/1988 | European Pat. Off. . |
| 0 404 190 | 12/1990 | European Pat. Off. . |
| 2581646 | 11/1986 | France . |
| 2606409 | 5/1988 | France . |

OTHER PUBLICATIONS

S.M. Rothman et al, *Annals of Neurology*, vol. 19, No. 2, 105–111 (1986).
M.N. Perkins et al, *Neuroscience Lett.*, 23, 333 (1981).
J. Davies et al, *Neuroscience Lett.*, 21, 77 (1981).
K. Matoba et al, "Structional Modification of Bioactive Compounds II. Synthesis of Aminophosphonic Acids", *Chem. Pharm. Bull.*, 32, (10), 3918–3925 (1984).
D.E. Murphy et al, *J. Pharmacol. Exp. Ther.*, 240, (3), 778–784 (1987).

Primary Examiner—Gary Geist
Assistant Examiner—Dwayne C. Jones
Attorney, Agent, or Firm—Joseph W. Bulock; J. Timothy Keane

[57] ABSTRACT

A class of imidazo[1,2-a]pyridinylalkyl phosphonic acid compounds is described for treatment to reduce neurotoxic injury associated with anoxia or ischemia which typically follows stroke, cardiac arrest or perinatal asphyxia. The treatment includes administration of a compound of this class alone or in a composition in an amount effective as an antagonist to inhibit excitotoxic actions at major neuronal excitatory amino acid receptor sites. Compounds of most interest are those of the formula:

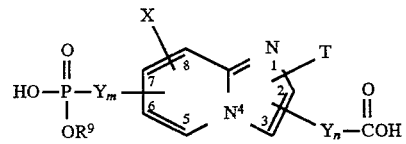

and the carboxylic and phosphonic alkyl esters and salts thereof; wherein $R^9$ is selected from hydrido, methyl, ethyl, n-propyl, isopropyl, n-butyl, isobutyl, sec-butyl, tert-butyl, cyclopropyl, cyclobutyl, cyclopentyl, cyclohexyl and cycloheptyl; wherein each of $Y_m$ and $Y_n$ is a spacer group independently selected methylene and ethylene radicals which may be unsubstituted and from methylene radicals which may be substituted with a group selected from halo, hydroxy and oxo;

wherein each of m and n is a number independently selected from zero to two, inclusive; wherein each X and T is one or more groups independently selected from hydrido, alkyl, cycloalkyl, halo, haloalkyl, hydroxy, hydroxyalkyl, alkoxy, alkoxyalkyl and alkanoyl; or a pharmaceutically-acceptable acid addition salt thereof.

23 Claims, No Drawings

IMIDAZO[1,2-A]PYRIDINYLALKYL PHOSPHONIC ACID COMPOUNDS FOR TREATMENT OF NEUROTOXIC INJURY

This is a Divisional of application Ser. No. 07/871,995 filed Dec. 9, 1991 now U.S. Pat. No. 5,360,796, which is a continuation of Ser. No. 07/445,228, filed Dec. 4, 1989 and abandoned on Dec. 9, 1991.

FIELD OF THE INVENTION

This invention is in the field of clinical neurology and relates specifically to a class of compounds, compositions and methods for neuro-protective purposes such as controlling chronic or acute neurotoxic injury or brain damage resulting from neuro-degenerative diseases. For example, these compounds are particularly useful for treating neurotoxic injury which follows periods of anoxia or ischemia associated with stroke, cardiac arrest or perinatal asphyxia. The compounds would also be useful as anticonvulsants and analgesics.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman et al, Annals of Neurology, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS). Glutamate is believed to be a mixed agonist capable of binding to and exciting all three receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia caused by stroke, cardiac arrest or perinatal asphyxia.

Aminophosphonic acids have been investigated as neurotransmitter blockers [see M. N. Perkins et al, Neuroscience Lett., 23, 333 (1981); and J. Davies et al, Neuroscience Lett., 21, 77 (1981)]. In particular, compounds such as 2-amino-4-(2-phosphonomethylphenyl)-butyric acid and 2-(2-amino-2-carboxy)ethylphenylphosphonic acid have been synthesized for evaluation as antagonists in blocking the action of the neurotransmitter compounds L-glutamic acid and L-aspartic acid [K. Matoba et al, "Structural Modification of Bioactive Compounds II. Syntheses of Aminophosphonic Acids", Chem. Pharm. Bull., 32, (10) 3918–3925 (1984)].

U.S. Pat. No. 4,657,899 to Rzeszotarski et al described a class of ω-[2-(phosphonoalkylenyl)phenyl]-2-aminoalkanoic acids characterized as being selective excitatory amino acid neurotransmitter receptor blockers. These compounds are mentioned for use as anticonvulsants, antiepileptics, analgesics and cognition enhancers. Typical compounds of the class include 3-[2-phosphonomethylphenyl]-2-aminopropanoic acid and 3-[2-(2-phosphonoethyl)phenyl]-2-aminopropanoic acid.

An analogue of 2-amino-7-phosphonaheptanoic acid, namely 3-(2-carboxypiperazin-4-yl)propyl-1-phosphonic acid [CPP], has been reported as a potent and selective NMDA antagonist in an evaluation of CPP binding to rat brain hippocamal tissue [D. E. Murphy et al, J. Pharmacol. Exp. Ther., 240 (3), 778–784 (1987)].

Several classes of imidazopyridine compounds are known having various pharmaceutical uses. For example, EP# 120,589 published 3 Oct. 1984 describes certain imidazo-(1,2-a)pyridinylheterocyclic compounds for use as cardiotonic and antiulcer agents. Schering EP# 33,094 published 5 Aug. 1981 describes 3,8-disubstituted-imidazo-(1,2-a) pyridine compounds for use as antisecretory and cytoprotective agents. Synthelabo U.S. Pat. No. 4,650,796 published 19 Feb. 1986 describes 2-phenyl-3-acylaminomethylimidazo pyridine compounds as anxiolytic, hypnotic and anticonvulsant agents. Synthelabo U.S. Pat. No. 4,501,745 describes imidazo-(1,2-a)-pyridinealkanoic acid derivatives as anxiolytic, hynotic and anticonvulsant agents. Schering U.S. Pat. No. 4,450,164 describes phosphonic acid derivatives of imidazo(1,2-a) pyridine compounds for use as treatment of gastrointestinal diseases such as ulcers.

Ciba-Geigy U.S. Pat. No. 4,746,653 describes phosphono-substituted 2-carboxy-2,3-dihydro or perhydroindolyl derivatives for use as NMDA antagonists to treat cerebral ischemia.

DESCRIPTION OF THE INVENTION

Control of neuropathological processes and the neurodegenerative consequences thereof in mammals is provided by treating a mammal susceptible to neurotoxic injury with an anti-excitotoxic effective amount of a compound characterized in having activity as an antagonist at a major neuronal excitatory amino acid receptor site, such as the NMDA receptor site. Such NMDA antagonist compounds may be selected from a class of imidazo[1,2a]pyridinealkyl phosphonic acid compounds defined by Formula I:

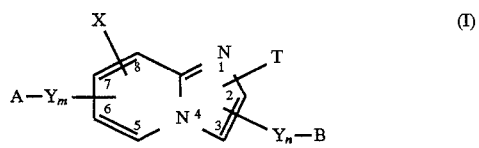

wherein each of A and B is an acidic moiety selected to contain at least one acidic hydrogen atom and wherein said acidic moiety is independently selected from carboxylic acid, tetrazole, phosphorus-containing acids, sulfur-containing acids, thio-phosphorus-containing acids and the amide, ester and salt derivatives of said acids;

wherein each of $Y_m$ and $Y_n$ is a spacer group independently selected from one or more of alkyl, cycloalkyl, cycloalkylalkyl, alkenyl, alkynyl, sulfinyl, sulfonyl, aryl, aralkyl, and heteroaryl, any one of which spacer groups may be substituted at any substitutable position with one or more groups selected from alkyl, cycloalkyl, cycloalkylalkyl, oxo, halo, haloalkyl, alkenyl, cycloalkenyl, alkynyl, alkoxycarbonyl, aryl, aralkyl, hydroxy, hydroxyalkyl, alkoxy, aryloxy, alkoxyalkyl, aralkoxy, aralkylthio, cyano, cyanoamino, nitro, alkanoyl, aroyl, mercapto, alkylthio, arylthio, alkylsulfinyl, arylsulfinyl, alkylsulfonyl, arylsulfonyl, heteroaryl, heteroarylalkyl, and saturated or partially unsaturated heterocylic and heterocyclicalkyl, and amino and amido radicals of the formula

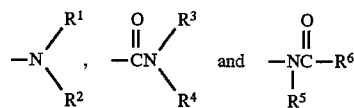

wherein each of $R^1$, $R^2$, $R^3$, $R^4$, $R^5$ and $R^6$ is independently selected from hydrido, alkyl, cycloalkyl, hydroxyalkyl, cycloalkylalkyl, alkoxyalkyl, aralkyl and aryl; and wherein $R^1$ and $R^2$ taken together, $R^3$ and $R^4$ taken together and $R^5$ and $R^6$ taken together may form a heterocyclic group having five to seven ring members including the nitrogen atom of said amino or amido radical and which heterocyclic group may further contain one or more hetero atoms as ring members selected from oxygen, nitrogen and sulfur and which heterocyclic group may be saturated or partially unsaturated; wherein $R^1$ and $R^2$ taken together and $R^3$ and $R^4$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur; wherein each of m and n is a number independently selected from zero to five, inclusive;

wherein each X and T is one or more groups independently selected from hydrido, alkyl, cycloalkyl, cycloalkylalkyl, oxo, halo, haloalkyl, alkenyl, cycloalkenyl, alkynyl, aryl, aralkyl, hydroxy, hydroxyalkyl, alkoxy, aryloxy, alkoxyalkyl, alkoxycarbonyl, aralkoxy, aralkylthio, cyano, cyanoamino, nitro, alkanoyl, mercapto, alkylthio, arylthio, alkylsulfinyl, arylsulfinyl, alkylsulfonyl, arylsulfonyl, heteroaryl, heteroarylalkyl, and saturated or partially unsaturated heterocylic and heterocyclicalkyl, and amino and amido radicals of the formula

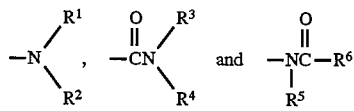

wherein each of $R^1$, $R^2$, $R^3$, $R^4$, $R^5$ and $R^6$ is independently selected from hydrido, alkyl, cycloalkyl, hydroxyalkyl, cycloalkylalkyl, alkoxyalkyl, aralkyl and aryl, and wherein $R^1$ and $R^2$ taken together, $R^3$ and $R^4$ taken together and $R^5$ and $R^6$ taken together may form a heterocyclic group having five to seven ring members including the nitrogen atom of said amino or amido radical and which heterocyclic group may further contain one or more hetero atoms as ring members selected from oxygen, nitrogen and sulfur and which heterocyclic group may be saturated or partially unsaturated; wherein $R^1$ and $R^2$ taken together and $R^3$ and $R^4$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur; or a pharmaceutically-acceptable salt thereof.

A preferred class consists of compounds within Formula I wherein each of A and B is an acidic moiety selected to contain at least one acidic hydrogen atom and wherein said acidic moiety is independently selected from carboxylic acid, tetrazole, sulfenic acid, sulfinic acid, sulfonic acid, and phosphorus-containing and thio-phosphorus-containing acids selected from

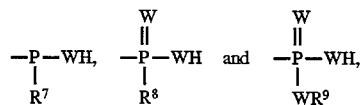

wherein each W is independently selected from oxygen atom and sulfur atom; wherein each of $R^7$, $R^8$ and $R^9$ is independently selected from hydrido, alkyl, cycloalkyl, cycloalkylalkyl, aryl and aralkyl; wherein each of $R^7$ and $R^8$ may be further independently selected from amino radical of the formula

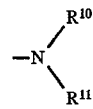

wherein each of $R^{10}$ and $R^{11}$ is independently selected from hydrido, alkyl, cycloalkyl, hydroxyalkyl, haloalkyl, cycloalkylalkyl, alkoxyalkyl, aralkyl and aryl, and wherein $R^{10}$ and $R^{11}$ taken together may form a heterocyclic group having five to seven ring members including the nitrogen atom of said amino radical and which heterocyclic group may further contain one or more hetero atoms as ring members selected from oxygen, nitrogen and sulfur and which heterocyclic group may be saturated or partially unsaturated; wherein $R^{10}$ and $R^{11}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur; wherein $R^7$ may be further independently selected from hydroxy, alkoxy, alkylthio, aryloxy, arylthio, aralkylthio and aralkoxy; and the amide, ester and salt derivatives of said acids; wherein each of $Y_m$ and $Y_n$ is a spacer group independently selected from one or more of alkyl, alkenyl, alkynyl, aryl and aralkyl, any one of which spacer groups may be substituted at any substitutable position with one or more groups selected from alkyl, cycloalkyl, cycloalkylalkyl, oxo, halo, haloalkyl, alkenyl, cycloalkenyl, alkynyl, alkoxycarbonyl, aryl, aralkyl, hydroxy, hydroxyalkyl, alkoxy, aryloxy, alkoxyalkyl, aralkoxy, cyano, cyanoamino, nitro, alkanoyl, aroyl, mercapto, alkylthio, arylthio, alkylsulfinyl, alkylsulfonyl, arylsulfinyl, arylsulfonyl, and amino and amido radicals of the formula

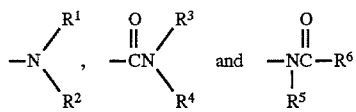

wherein each of $R^1$, $R^2$, $R^3$, $R^4$, $R^5$ and $R^6$ is independently selected from hydrido, alkyl, cycloalkyl, hydroxyalkyl, cycloalkylalkyl, alkoxyalkyl, phenalkyl and phenyl and wherein $R^1$ and $R^2$ taken together, $R^3$ and $R^4$ taken together and $R^5$ and $R^6$ taken together may form a heterocyclic group having five to seven ring members including the nitrogen atom of said amino or amido radical and which heterocyclic group may further contain one or more hetero atoms as ring members selected from oxygen, nitrogen and sulfur and which heterocyclic group may be saturated or a partially unsaturated; wherein $R^1$ and $R^2$ taken together and $R^3$ and $R^4$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur; wherein each of m and n is a number independently selected from zero to four, inclusive;

wherein each X and T is one or more groups independently selected from hydrido, alkyl, cycloalkyl, cycloalkylalkyl, halo, haloalkyl, alkenyl, cycloalkenyl, alkynyl, aryl, aralkyl, hydroxy, hydroxyalkyl, alkoxy, aryloxy, alkoxyalkyl, aralkoxy, cyano, cyanoamino, nitro, alkanoyl, mercapto, alkylthio, arylthio, alkylsulfinyl, alkylsulfonyl, arylsulfinyl, arylsulfonyl, and amino and amido radicals of the formula

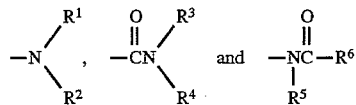

wherein each of $R^1$, $R^2$, $R^3$, $R^4$, $R^5$ and $R^6$ is independently selected from hydrido, alkyl, cycloalkyl, hydroxyalkyl, cycloalkylalkyl, alkoxyalkyl, phenalkyl and phenyl and wherein $R^1$ and $R^2$ taken together, $R^3$ and $R^4$ taken together and $R^5$ and $R^6$ taken together may form a heterocyclic group having five to seven ring members including the nitrogen atom of said amino or amido radical and which heterocyclic group may further contain one or more hetero atoms as ring members selected from oxygen, nitrogen and sulfur and which heterocyclic group may be saturated or partially unsaturated; wherein $R^1$ and $R^2$ taken together and $R^3$ and $R^4$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur; or a pharmaceutically-acceptable acid addition salt thereof.

A more preferred class consists of compounds within Formula I wherein each of A and B is an acidic moiety selected to contain at least one acidic hydrogen atom and wherein said acidic moiety is independently selected from carboxylic acid, tetrazole and sulfonic acid, and selected from phosphinous acids, phosphonous acids and phosphonic acids of the formula

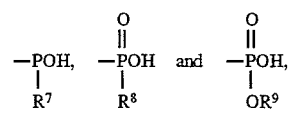

wherein each of $R^7$, $R^8$ and $R^9$ is independently selected from hydrido, alkyl, cycloalkyl, cycloalkylalkyl, phenyl, phenalkyl and wherein each of $R^7$ and $R^8$ may be further independently selected from amino radical of the formula

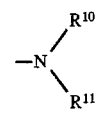

wherein each of $R^{10}$ and $R^{11}$ is independently selected from hydrido, alkyl, cycloalkyl, hydroxyalkyl, haloalkyl, cycloalkylalkyl, alkoxyalkyl, aralkyl and aryl, and wherein $R^{10}$ and $R^{11}$ taken together may form a heterocyclic group having five to seven ring members including the nitrogen atom of said amino radical and which heterocyclic group may further contain one or more hetero atoms as ring members selected from oxygen, nitrogen and sulfur and which heterocyclic group may be saturated or partially unsaturated; wherein $R^{10}$ and $R^{11}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur; wherein $R^7$ is further selected from hydroxy, alkoxy, phenoxy, benzyloxy, benzylthio, mercapto, alkylthio and phenylthio; and the monoalkylamide, dialkylamide, alkylester and salt derivatives of said acids;

wherein each of $Y_m$ and $Y_n$ is a spacer group independently selected from one or more of alkyl, alkenyl, alkynyl, aryl and aralkyl, any one of which spacer groups may be substituted at any substitutable position with one or more groups selected from alkyl, cycloalkyl, cycloalkylalkyl, oxo, halo, haloalkyl, alkenyl, cycloalkenyl, alkynyl, phenyl, benzyl, hydroxy, hydroxyalkyl, alkoxy, phenoxy, alkoxyalkyl, benzyloxy, cyano, cyanoamino, nitro, alkanoyl, benzoyl, mercapto, alkylthio, arylthio, alkylsulfinyl, alkylsulfonyl, arylsulfinyl, arylsulfonyl, and amino and amido radicals of the formula

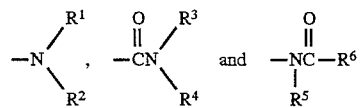

wherein each of $R^1$, $R^2$, $R^3$, $R^4$, $R^5$ and $R^6$ is independently selected from hydrido, alkyl, cycloalkyl, hydroxyalkyl, alkoxyalkyl, benzyl, phenyl, and wherein $R^1$ and $R^2$ taken together, $R^3$ and $R^4$ taken together and $R^5$ and $R^6$ taken together may for a heterocyclic group having five ring members including the nitrogen atom of said amino or amido radical and which heterocyclic group may further contain one or more hetero atoms as ring members selected from oxygen, nitrogen and sulfur and which heterocyclic group may be saturated or partially unsaturated;

wherein $R^1$ and $R^2$ taken together and $R^3$ and $R^4$ taken together may form an aromatic heterocyclic group having five to seven ring members including the nitrogen atom of said amino or amido radical and which aromatic heterocyclic group may further contain one or more hetero atoms as ring atoms selected from oxygen, nitrogen and sulfur; wherein each of m and n is a number independently selected from zero to three, inclusive;

wherein each X and T is one or more groups independently selected from hydrido, alkyl, cycloalkyl, cycloalkylalkyl, halo, haloalkyl, alkenyl, cycloalkenyl, alkynyl, phenyl, benzyl, hydroxy, hydroxyalkyl, alkoxy, phenoxy, alkoxyalkyl, benzyloxy, cyano, cyanoamino, nitro, alkanoyl, mercapto, alkylthio, arylthio, alkylsulfinyl, alkylsulfonyl, arylsulfinyl, arylsulfonyl, and amino and amido radicals of the formula

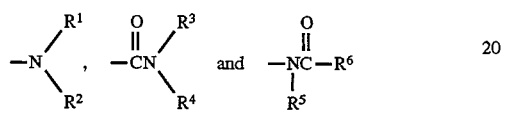

wherein each of $R^1$, $R^2$, $R^3$, $R^4$, $R^5$ and $R^6$ is independently selected from hydrido, alkyl, cycloalkyl, hydroxyalkyl, alkoxyalkyl, benzyl and phenyl; and wherein $R^1$ and $R^2$ taken together, $R^3$ and $R^4$ taken together and $R^5$ and $R^6$ taken together may form a heterocyclic group having five to seven ring members including the nitrogen atom of said amino or amido radical and which heterocyclic group may further contain one or more hetero atoms as ring members selected from oxygen, nitrogen and sulfur and which heterocyclic group may be saturated or partially unsaturated; wherein $R^1$ and $R^2$ taken together and $R^3$ and $R^4$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur; or a pharmaceutically-acceptable acid addition salt thereof.

An even more preferred class consists of compounds within Formula I wherein each of A and B is an acidic moiety selected to contain at least one acidic hydrogen atom and wherein said acidic moiety is independently selected from carboxylic acid and tetrazole, and selected from phosphonous acids and phosphonic acids of the formula

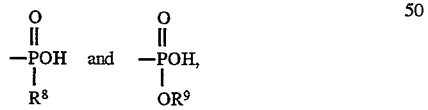

wherein each of $R^8$ and $R^9$ is independently selected from hydrido, alkyl, cycloalkyl, cycloalkylalkyl, phenyl and benzyl and wherein $R^8$ is further selected from amino radical of the formula

wherein each of $R^{10}$ and $R^{11}$ is independently selected from hydrido, alkyl, cycloalkyl, cycloalkylalkyl, phe-nyl and benzyl, and wherein $R^{10}$ and $R^{11}$ taken together may form a heterocyclic group having five to seven ring members including the nitrogen atom of said amino radical and which heterocyclic group may further contain one or more hetero atoms as ring members selected from oxygen, nitrogen and sulfur and which heterocyclic group may be saturated or partially unsaturated; wherein $R^{10}$ and $R^{11}$ taken together and $R^3$ and $R^4$ taken together may form an aromatic heterocyclic group having five ring members including the nitrogen atom of said amino radical and which aromatic heterocyclic group may further contain one or more hetero atoms as ring atoms selected from oxygen, nitrogen and sulfur; and the monoalkylamide, dialkylamide, alkylester and salt derivatives of said acids;

wherein each of $Y_m$ and $Y_n$ is a spacer group independently selected from one or more of alkyl, alkenyl, alkynyl, aryl and aralkyl, any one of which spacer groups may be substituted at any substitutable position with one or more groups selected from alkyl, cycloalkyl, oxo, halo, haloalkyl, phenyl, benzyl, hydroxy, hydroxyalkyl, alkoxy, phenoxy, alkoxyalkyl, benzyloxy, cyano, alkanoyl, and amino and amido radicals of the formula

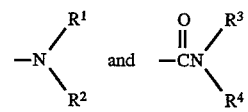

wherein each of $R^1$, $R^2$, $R^3$ and $R^4$ is independently selected from hydrido, alkyl, phenyl and benzyl; wherein each of m and n is a number independently selected from zero to three, inclusive;

wherein each X and T is one or more groups independently selected from hydrido, alkyl, cycloalkyl, cycloalkylalkyl, halo, haloalkyl, alkenyl, cycloalkenyl, alkynyl, phenyl, benzyl, hydroxy, hydroxyalkyl, alkoxy, alkoxyalkyl, benzyloxy, cyano, cyanoamino, alkanoyl, mercapto, alkylthio, arylthio, alkylsulfinyl, alkylsulfonyl, arylsulfinyl and arylsulfonyl, and amino and amido radicals of the formula

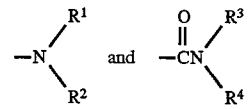

wherein each of $R^1$, $R^2$, $R^3$ and $R^4$ is independently selected from hydrido, alkyl, phenyl and benzyl; or a pharmaceutically-acceptable acid addition salt thereof.

A highly preferred class of compounds consists of those within Formula I wherein A is selected from phosphonic acids of the formula

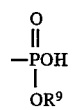

wherein $R^9$ is selected from hydrido, alkyl, cycloalkyl, phenyl and benzyl; wherein A is further selected from the full alkyl esters and metal salts of the phosphonic acids of said formula; wherein B is independently selected from carboxylic acid and alkyl ester and salts thereof;

wherein each of $Y_m$ and $Y_n$ is a spacer group independently selected from one or more groups of the formula

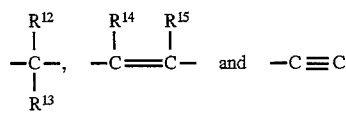

wherein each of $R^{12}$ and $R^{13}$ is independently selected from hydrido, alkyl, cycloalkyl, halo, haloalkyl, phenyl, benzyl, hydroxy, hydroxyalkyl, alkoxy, phenoxy, alkoxyalkyl, benzyloxy, cyano, alkanoyl,

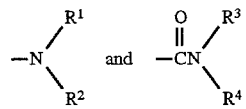

wherein each of $R^1$, $R^2$, $R^3$ and $R^4$ is independently selected from hydrido, alkyl and phenyl; wherein $R^{12}$ and $R^{13}$ may be taken together to form oxo; wherein each of $R^{14}$ and $R^{15}$ is independently selected from hydrido, alkyl, haloalkyl, phenyl, hydroxyalkyl and alkoxyalkyl; wherein each of m and n is a number independently selected from zero to three, inclusive;

wherein each X and T is one or more groups independently selected from hydrido, alkyl, cycloalkyl, cycloalkylalkyl, halo, haloalkyl, alkenyl, cycloalkenyl, alkynyl, phenyl, benzyl, hydroxy, hydroxyalkyl, alkoxy, phenoxy, alkoxyalkyl, benzyloxy, cyano, cyanoamino, alkanoyl, mercapto, alkylthio, arylthio, alkylsulfinyl, alkylsulfonyl, arylsulfinyl and arylsulfonyl,

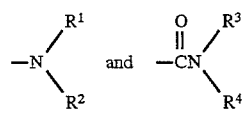

wherein each of $R^1$, $R^2$, $R^3$ and $R^4$ is independently selected from hydrido, alkyl and phenyl; or a pharmaceutically-acceptable acid addition salt thereof.

A more highly preferred class consists of compounds within Formula I wherein A is selected from phosphonic acids of the formula

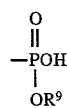

wherein $R^9$ is selected from hydrido, methyl, ethyl, n-propyl, isopropyl, n-butyl, isobutyl, sec-butyl, tert-butyl, cyclopropyl, cyclobutyl, cyclopentyl, cyclohexyl and cycloheptyl; wherein A is further selected from the full alkyl esters and salts of the phosphonic acids of said formula; wherein B is independently selected from carboxylic acid and alkyl esters and salts thereof;

wherein each of $Y_m$ and $Y_n$ is a spacer group independently selected from one or more methylene and ethylene radicals of the formula

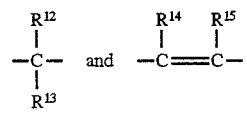

wherein each of $R^{12}$ and $R^{13}$ is independently selected from hydrido, alkyl, cycloalkyl, halo, haloalkyl, hydroxy, hydroxyalkyl, alkoxy, alkoxyalkyl, alkanoyl,

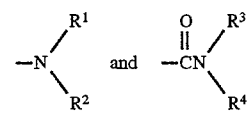

wherein each of $R^1$, $R^2$, $R^3$ and $R^4$ is independently selected from hydrido, alkyl and phenyl; wherein $R^{12}$ and $R^{13}$ may be taken together to form oxo; wherein each of $R^{14}$ and $R^{15}$ is independently selected from hydrido, alkyl, haloalkyl, phenyl, hydroxyalkyl and alkoxyalkyl; wherein each of m and n is a number independently selected from zero to three, inclusive;

wherein each X and T is one or more groups independently selected from hydrido, alkyl, cycloalkyl, halo, haloalkyl, phenyl, benzyl, hydroxy, hydroxyalkyl, alkoxy, phenoxy, alkoxyalkyl, benzyloxy, alkanoyl,

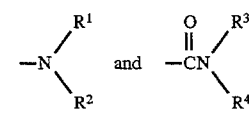

wherein each of $R^1$, $R^2$, $R^3$ and $R^4$ is independently selected from hydrido and alkyl; or a pharmaceutically-acceptable acid addition salt thereof.

An even more highly preferred class consists of compounds of Formula II:

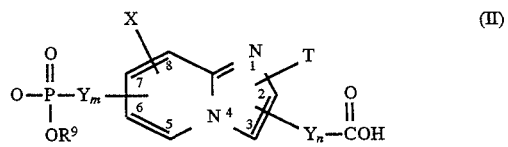

(II)

and the carboxylic and phosphonic alkyl esters and salts thereof; wherein $R^9$ is selected from hydrido, methyl, ethyl, n-propyl, isopropyl, n-butyl, isobutyl, sec-butyl, tert-butyl, cyclopropyl, cyclobutyl, cyclopentyl, cyclohexyl and cycloheptyl; wherein each of $Y_m$ and $Y_n$ is a spacer group independently selected from one or more methylene and ethylene radicals of the formula

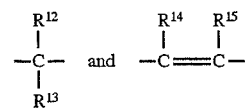

wherein each of $R^{12}$ and $R^{13}$ is independently selected from hydrido, alkyl, halo, haloalkyl, hydroxy, hydroxyalkyl, alkoxy, alkoxyalkyl and alkanoyl; wherein $R^{12}$ and $R^{13}$ may be taken together to form oxo; wherein each of $R^{14}$ and $R^{15}$ is independently selected from hydrido, alkyl, haloalkyl, hydroxyalkyl and alkoxyalkyl; wherein each of m and n is a number independently selected from zero to two, inclusive;

wherein each X and T is one or more groups independently selected from hydrido, alkyl, cycloalkyl, halo, haloalkyl, hydroxy, hydroxyalkyl, alkoxy, alkoxyalkyl, and alkanoyl; or a pharmaceutically-acceptable acid addition salt thereof.

Especially preferred of this family of Formula II compounds are those wherein each of $Y_m$ and $Y_n$ is independently selected from methylene and ehtylene radicals which may be unsubstituted and from methylene radicals substituted with a group selected from halo, hydroxy and oxo.

Specific compounds of particular interest within Formula II are the following:

ethyl 5-[(diethoxyphosphinyl)methyl]imidazo[1,2-a]pyridine-2-carboxylate;
5-(phosphonomethyl)imidazo[1,2-a]pyridine-2-carboxylic acid;
ethyl 6-[(diethoxyphosphinyl)methyl]imidazo[1,2-a]pyridine-2-carboxylate;
6-(phosphonomethyl)imidazo[1,2-a]pyridine-2-carboxylic acid;
ethyl 7-[(diethoxyphosphinyl)methyl]imidazo[1,2-a]pyridine-2-carboxylate;
7-(phosphonomethyl)imidazo[1,2-a]pyridine-2-carboxylic acid;
ethyl 8-[(diethoxyphosphinyl)methyl]imidazo[1,2-a]pyridine-2-carboxylate;
8-(phosphonomethyl)imidazo[1,2-a]pyridine-2-carboxylic acid;
ethyl 6-chloro-5-[(diethoxyphosphinyl)methyl]imidazo[1,2-a]pyridine-2-carboxylate;
6-chloro-5-(phosphonomethyl)imidazo[1,2-a]pyridine-2-carboxylic acid;
ethyl 7-chloro-5-[(diethoxyphosphinyl)methyl]imidazo[1,2-a]pyridine-2-carboxylate;
7-chloro-5-(phosphonomethyl)imidazo[1,2-a]pyridine-2-carboxylic acid;
ethyl 5-[(diethoxyphosphinyl)methyl]-7-methoxyimidazo[1,2-a]pyridine-2-carboxylate;
7-methoxy-5-(phosphonomethyl)imidazo[1,2-a]pyridine-2-carboxylic acid;
ethyl 8-(diethoxyphosphinyl)-5-methylimidazo[1,2-a]pyridine-2-carboxylate;
5-methyl-8-phosphonoimidazo[1,2-a]pyridine-2-carboxylic acid;
ethyl 5-(diethoxyphosphinyl)imidazo[1,2-a]pyridine-2-carboxylate;
ethyl 5-(diethoxyphosphinyl)imidazo[1,2-a]pyridine-2-carboxylate, monohydrochloride;
5-phosphonoimidazo[1,2-a]pyridine-2-carboxylic acid;
ethyl 5-[(diethoxyphosphinyl)hydroxymethyl]imidazo[1,2-a]pyridine-2-carboxylate;
ethyl 5-[(diethoxyphosphinyl)hydroxymethyl]imidazo[1,2-a]pyridine-2-carboxylate, monohydrochloride;
5-(hydroxyphosphonomethyl)imidazo[1,2-a]pyridine-2-carboxylic acid, monohydrochloride;
ethyl 5-[2-(diethoxyphosphinyl)-E-ethenyl]imidazo[1,2-a]pyridine-2-carboxylate;
5-(2-phosphono-E-ethenyl)imidazo[1,2-a]pyridine-2-carboxylic acid;
5-(2-phosphonoethyl)imidazo[1,2-a]pyridine-2-carboxylic acid;
ethyl 8-[(diethhoxyphosphinyl)methyl]-3-methylimidazo[1,2-a]pyridine-2-carboxylate;
ethyl 8-[(diethoxyphosphinyl)methyl]-3-methylimidazo[1,2-a]pyridine-2-carboxylate;
3-methyl-8-(phosphonomethyl)imidazo[1,2-a]pyridine-2-carboxylic acid, monohydrochloride;
ethyl 5-[(diethoxyphosphinyl)methyl]imidazo[1,2-a]-pyridine-3-carboxylate;
5-(phosphonomethyl)imidazo[1,2-a]pyridine-3-carboxylic acid;
6-(phosphonomethyl)imidazo[1,2-a]pyridine-3-carboxylic acid;
8-(phosphonomethyl)imidazo[1,2-a]pyridine-3-carboxylic acid;
ethyl 7-[(diethoxyphosphinyl)methyl]imidazo[1,2-a]pyridine-3-carboxylate;
7-(phosphonomethyl)imidazo[1,2-a]pyridine-3-carboxylic acid;
ethyl 6-chloro-5-[(diethoxyphosphinyl)methyl]imidazo[1,2-a]pyridine-3-carboxylate;
6-chloro-5-(phosphonomethyl)imidazo[1,2-a]pyridine-3-carboxylic acid;
ethyl 5-[(diethoxyphosphinyl)methyl]-7-methoxy-imidazo[1,2-a]pyridine-3-carboxylate;
7-methoxy-5-(phosphonomethyl)imidazo[1,2-a]pyridine-3-carboxylic acid;
ethyl 7-chloro-5-[(diethoxyphosphinyl)methyl]imidazo[1,2-a]pyridine-3-carboxylate;
7-chloro-5-(phosphonomethyl)imidazo[1,2-a]pyridine-3-carboxylic acid;
ethyl 8-(diethoxyphosphinyl)-5-methylimidazo[1,2-a]pyridine-3-carboxylate;
5-methyl-8-phosphonoimidazo[1,2-a]pyridine-3-carboxylic acid;
ethyl 5-(diethoxyphosphinyl)imidazo[1,2-a]pyridine-3-carboxylate;
5-phosphonoimidazo[1,2-a]pyridine-3-carboxylic acid;
ethyl 5-[2-(diethoxyphosphinyl)-E-ethenyl]imidazo[1,2-a]pyridine-3-carboxylate;
5-(2-phosphono-E-ethenyl)imidazo[1,2-a]pyridine-3-carboxylic acid;
5-(2-phosphonoethyl)imidazo[1,2-a]pyridine-3-carboxylic acid;
ethyl 5-[(diethoxyphosphinyl)hydroxymethyl]imidazo[1,2-a]pyridine-3-carboxylate;
5-(hydroxyphosphonomethyl)imidazo[1,2-a]pyridine-3-carboxylic acid;
5-(fluorophosphonomethyl)imidazo[1,2-a]pyridine-3-carboxylic acid;
the alkyl esters and salts of the phosphonic acid groups and carboxylic acid groups of said compounds; and the pharmaceutically-acceptable acid addition salts thereof.

Specific compounds of more particular interest within Formula I are the following:

ethyl 5-[(diethoxyphosphinyl)methyl]imidazo[1,2-a]pyridine-2-carboxylate;
5-(phosphonomethyl)imidazo[1,2-a]pyridine-2-carboxylic acid;
6-(phosphonomethyl)imidazo[1,2-a]pyridine-2-carboxylic acid;
ethyl 7-[(diethoxyphosphinyl)methyl]imidazo[1,2-a]pyridine-2-carboxylate;
7-(phosphonomethyl)imidazo[1,2-a]pyridine-2-carboxylic acid;
8-(phosphonomethyl)imidazo[1,2-a]pyridine-2-carboxylic acid;
ethyl 6-chloro-5-[(diethoxyphosphinyl)methyl]imidazo[1,2-a]pyridine-2-carboxylate;
6-chloro-5-(phosphonomethyl)imidazo[1,2-a]pyridine-2-carboxylic acid;
5-methyl-8-phosphonoimidazo[1,2-a]pyridine-2-carboxylic acid;
5-phosphonoimidazo[1,2-a]pyridine-2-carboxylic acid;
ethyl 5-[(diethoxyphosphinyl)hydroxymethyl]imidazo[1,2-a]pyridine-2-carboxylate, monohydrochloride;

5-(hydroxyphosphonomethyl)imidazo[1,2-a]pyridine-2-carboxylic acid, monohydrochloride;

ethyl 8-[(diethoxyphosphinyl)methyl]-3-methylimidazo[1,2-a]pyridine-2-carboxylate;

3-methyl-8-(phosphonomethyl)imidazo[1,2-a]pyridine-2-carboxylic acid, monohydrochloride;

the alkyl esters and salts of the phosphonic acid and carboxylic acid groups of said compounds; and the pharmaceutically-acceptable acid addition salts thereof.

The term "hydrido" denotes a single hydrogen atom (H) which may be attached, for example, to a carbon atom to form hydrocarbyl or methylene, for example, or attached to an oxygen atom to form a hydroxyl group. Where the term "alkyl" is used, either alone or within other terms such as "haloalkyl", "aralkyl" and "hydroxyalkyl", the term "alkyl" embraces linear or branched radicals having one to about ten carbon atoms. Preferred alkyl radicals are "lower alkyl" radicals having one to about five carbon atoms. The term "cycloalkyl", embraces radicals having three to ten carbon atoms, such as cyclopropyl and cyclobutyl. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as bromochloromethyl group. Examples of a polyhaloalkyl are trifluoromethyl, 2,2,2-trifluoroethyl, perfluoroethyl and 2,2,3,3-tetrafluoropropyl groups. The term "aryl" embraces aromatic radicals such as phenyl, biphenyl and naphthyl. The term "aralkyl" embraces aryl-substituted alkyl radicals such as benzyl, diphenylmethyl and triphenylmethyl. The terms "benzyl" and "phenylmethyl" are interchangeable. The term "alkoxy" embraces linear or branched oxy-containing radicals having an alkyl portion of one to about ten carbon atoms, such as methoxy, ethoxy, isopropoxy and butoxy. The term "alkylthio" embraces radicals containing a linear or branched alkyl group of one to about ten carbon atoms attached to a divalent sulfur atom, such as a methythio group. The terms "aryloxy" and "arylthio" denote, respectively, aryl groups having an oxygen or sulfur atom through which the radical is attached to a nucleus, examples of which are phenoxy and phenylthio. The terms "sulfinyl" and "sulfonyl", whether used alone or linked to other terms, denote respectively, divalent radicals

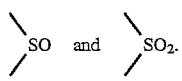

The term "acyl" whether used alone, or within a term such as acyloxy, denotes a radical provided by the residue remaining after removal of hydroxy from an organic acid, examples of such radical being acetyl and benzoyl. The term "alkenyl" embraces linear or branched radicals having two to about twenty carbon atoms, preferably three to about ten carbon atoms, and containing at least one carbon-carbon double bond. The term "alkynyl" embraces linear or branched radicals having two to about twenty carbon atoms, preferably two to about ten carbon atoms, and containing at least one carbon-carbon triple bond. The terms "cycloalkenyl" and "cycloalkynyl" embrace cyclic radicals having three to about ten ring carbon atoms including, respectively, one or more double or triple bonds involving adjacent ring carbons. The terms "alkoxy" and "alkoxyalkyl" embrace linear or branched oxy-containing radicals each having alkyl portions of one to about ten carbon atoms, such as methoxy group. The "alkoxy" or alkoxyalkyl" radicals may be further substituted with one or more halo atoms, such as fluoro, chloro or bromo, to provide haloalkoxy or haloalkoxyalkyl groups. The terms "heteroaryl", "aromatic heterocyclic group" and "fully-unsaturated heterocyclic group" embrace aromatic ring systems containing one to four hetero atoms selected from oxygen, nitrogen and sulfur in a ring system having five or six ring members which may include the nitrogen atom of an amino or amidoradical (as mentioned in the foregoing description). Examples of such "heteroaryl" groups are thienyl, furanyl, pyridinyl, thiazolyl, pyrimidyl, isoazolyl and the following structures:

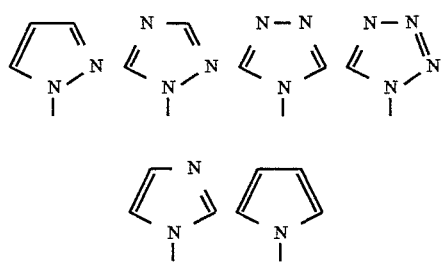

Examples of heterocyclic groups, which may be saturated or partially unsaturated and having five to seven ring members including the nitrogen atom of amino or amido radical (as mentioned in the foregoing description) are the following:

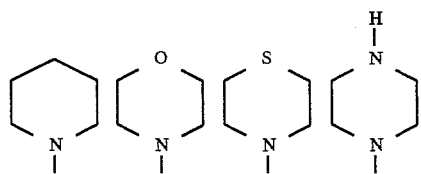

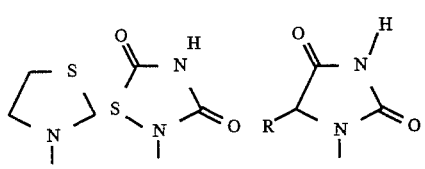

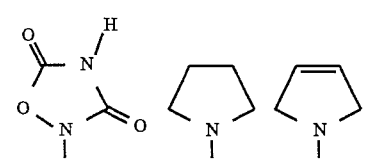

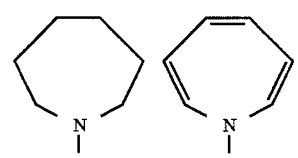

Also embraced within the foregoing definitions are fused ring radicals, i.e., radicals having two or more fused rings either or both of which may be saturated, partially unsaturated or fully unsaturated, examples of which are the following:

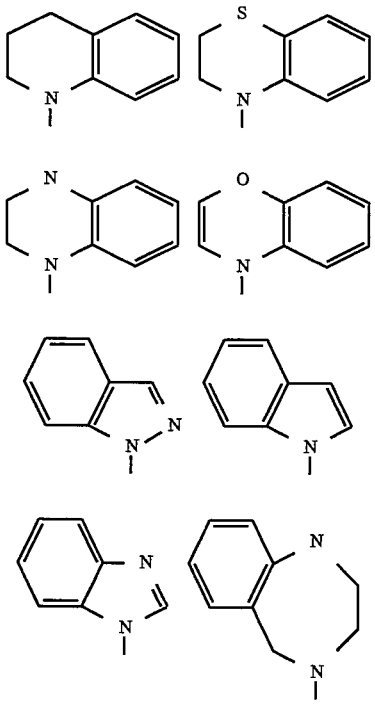

The terms "heteroaryl" and "saturated or partially unsaturated heterocyclic" are also specified as possible selections for the X, T and Y substituents of Formula I and Formula II compounds of this invention. Examples of such terms are as illustrated above for the hetero-containing groups which incorporate an amino or amido radical nitrogen atom within the heteroaryl or heterocyclic group. Where the terms "heteroaryl" and "saturated or partially unsaturated heterocyclic" are specified as selections for X, T and Y, it is understood that such terms are construed in light of the foregoing description and exemplifications, with the exception that any of the specified groups may be attached at the X, Y and T positions any attachable position on the group, including the amino or amido radical nitrogen atom. Any of these groups may be attached at the X, T and Y positions through an alkyl group. Thus, "heteroarylalkyl" would be exemplified by imidazolemethyl.

Within this class of compounds of the invention are the pharmaceutically acceptable salts of the compounds of Formula I and Formula II, including acid addition salts and base addition salts. The term "pharmaceutically-acceptable salts" embraces "pharmacologically-acceptable salts" commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I and Formula II may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I and Formula II include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I and Formula II by reacting, for example, the appropriate acid or base with the compound of Formula I and Formula II.

Compounds of general Formula I and Formula II can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I and Formula II with an optically pure acid in an activated form or an optically pure isocyanate. The synthesized diastereoisomers can be separated by conventional means such as chromatography, distillation, crystallization or sublimation, and then hydrolyzed to deliver the enantiomericaly pure compound. The optically active compounds of Formula I and Formula II can likewise be obtained by utilizing optically active starting materials. These isomers may be in the form of a free acid, a free base, an ester or a salt.

General Synthetic Procedures

Compounds embraced by Formula I and Formula II may be prepared in accordance with Schemes I–IV which follow:

Scheme I:

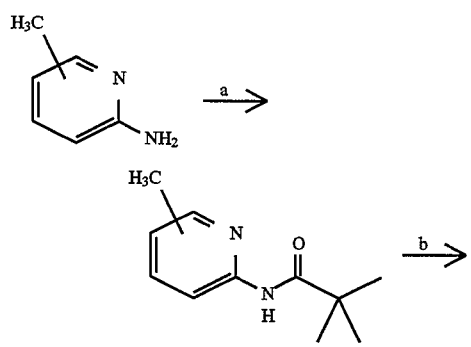

Scheme I:

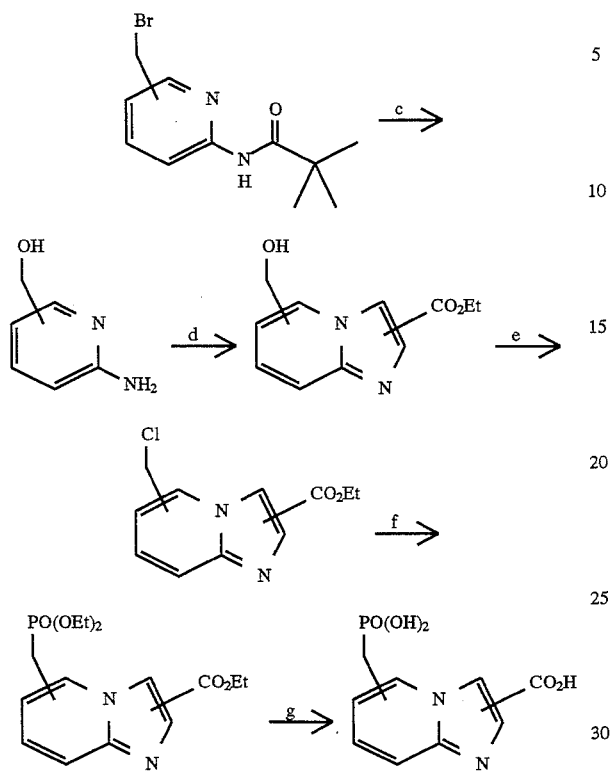

Scheme II:

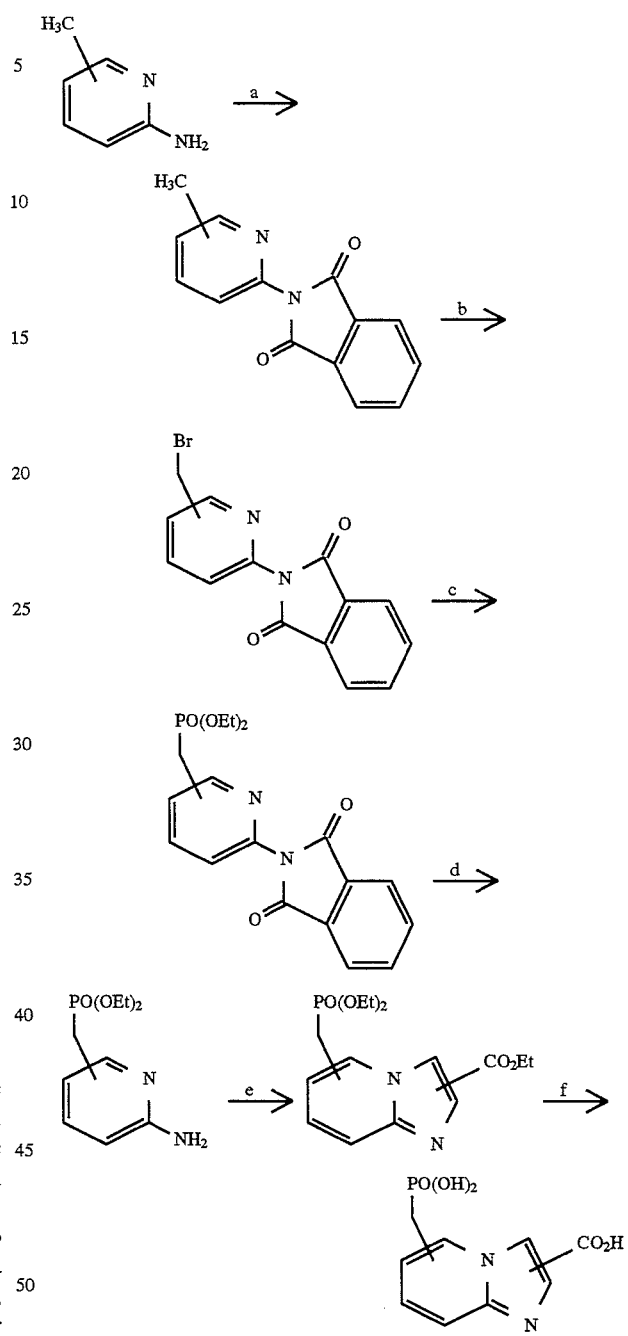

The amine of alkyl substituted 2-aminopyridines of Step (a) is protected as its pivaloyl derivative by reacting these amines with a slight excess of trimethylacetyl chloride in the presence triethylamine. This reaction is carried out in a chlorocarbon solvent such as $CHCl_3$ and $CH_2Cl_2$ at temperatures between 0° C. and room temperature (r.t.). This product in Step (b) is then brominated in the benzylic position in a chlorocarbon solvent such as $CCl_4$ using an equivalent of N-bromosuccinimide (NBS) and a catalytic amount of 2,2'-azobisisobutyronitrile (AIBN). The reaction is carried out under a reflector spot lamp at solvent reflux. The product of this reaction in Step (c) is refluxed with 5 to 25% aqueous sulfuric acid providing the hydroxylated 2-aminopyridines. The material is subsequently, Step (d), cyclized with an equivalent of either ethyl bromopyruvate or α-chloroformylacetate at r.t. in solvents such as ethylene glycol dimethylether (DME) or dioxane. The resulting intermediate is then refluxed in ethanol (EtOH) for several hours completing the cyclization. The benzylic hydroxyl function of the product imidazopyridine in Step (e) is converted to the chloride by reaction with a slight excess of thionylchloride ($SOCl_2$) at r.t. in a chlorocarbon solvent. Treatment of this benzylic chloride compound, Step (f), with an excess of triethyl phosphite in refluxing methyl ethyl ketone (MEK) containing a catalytic amount of sodium iodide produces the imidazopyridine phosphinate ester. A six to twelve hour reflux of this triester as indicated in Step (g) in from 2 to 6N hydrochloric acid (HCl) yields to imidazopyridine phosphonic-carboxylic acid product.

The amine of alkyl substituted 2-aminopyridines of Step (a) is protected as its phthaloyl derivative by mixing these amines with an equivalent of phthalic anhydride. This mixture is heated neat at temperatures between 180° and 200° C. This product is then brominated, Step (b), in the benzylic position in a chlorocarbon solvent such as $CCl_4$ using an equivalent of N-bromosuccinimide (NBS) and a catalytic amount of 2,2'-azobisosobutyronitrile (AIBN). The reaction is carried out under a reflector spot lamp at solvent reflux. Treatment of the benzylic bromide compound, Step (c), with an excess of triethyl phosphite in refluxing methyl ethyl ketone (MEK) containing a catalytic amount of potassium iodide (KI) produces the phosphinate ester. The product of the preceding action dissolved in a chlorocarbon solvent such as $CH_2Cl_2$ or $CHCl_3$, Step (d), is stirred with at least 3 equivalents of hydrazine monohydrate for several hours at ambient temperature. The product of this reaction is subsequently cyclized, Step (e), with an equivalent of either ethyl bromopyruvate or α-chloroformylacetate at r.t. in solvents such as ethylene glycol dimethylether (DME) or dioxane. The initial intermediate is then refluxed in ethanol (EtOH) for several hours completing the cyclization. A six to twelve hour reflux of this triester as indicated in Step (f) in from 2 to 6N hydrochloric acid (HCl) yields to imidazopyridine phosphonic-carboxylic acid product.

Scheme III:

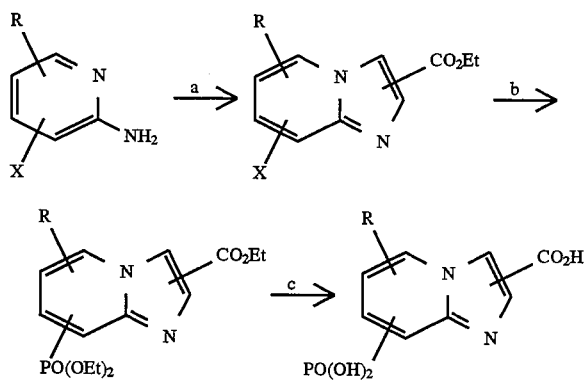

Scheme III:

X = halogen;
R = alkyl(s)

The alkyl halo-2-aminopyridine of Step (a) cyclized with an equivalent of either ethyl bromopyruvate or α-chloroformylacetate at ambient temperature in solvents such as ethylene glycol dimethylether (DME) or dioxane. The resulting intermediate is then refluxed in ethanol (EtOH) for several hours completing the cyclization. This halo-imidazopyridine product is, in Step (b), treated with 3 equivalents of diethylphosphite dissolved in an aromatic hydrocarbon solvent such as benzene or toluene. To this solution is added a catalytic amount of tetrakis (triphenylphosphine) Palladium (0) and one equivalent of triethylamine. The desired material is obtained following a 20 to 30 hour reflux of the reaction mixture. As indicated in Step (c), a six to twelve hour reflux of the triester in from 2 to 6N hydrochloric acid (HCl) provides the imidazopyridine phosphonic-carboxylic acid product.

Scheme IV:

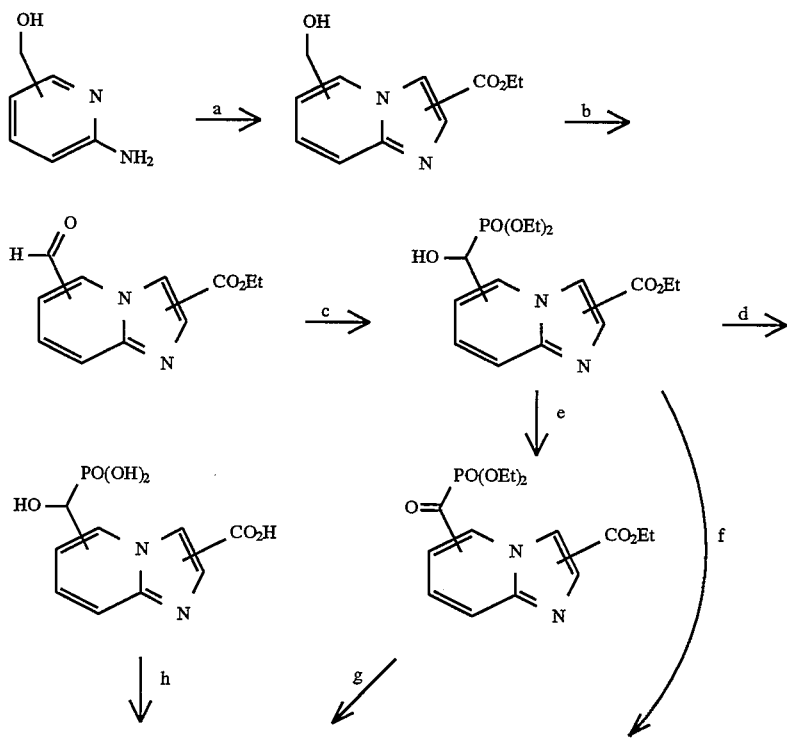

-continued
Scheme IV:

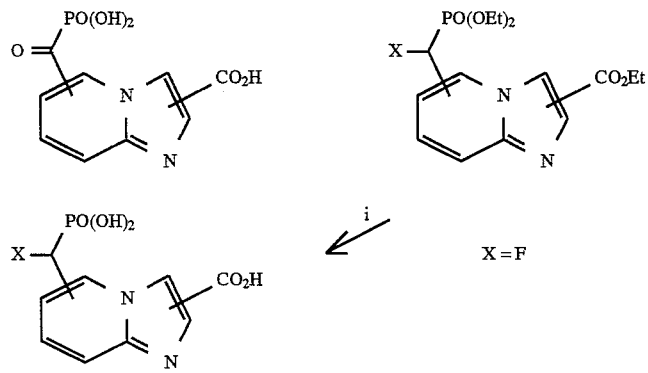

X = F

A hydroxyalkyl 2-aminopyridine is cyclized as illustrated in Step (a) with an equivalent of either ethyl bromopyruvate or α-chloroformylacetate at r.t. in solvents such as ethylene glycol dimethylether (DME) or dioxane. The resulting intermediate is then refluxed in ethanol (EtOH) for several hours completing the cyclization. Pyridinium chlorochromate oxidation this product, Step (b), in a chlorocarbon solvent such as $CH_2Cl_2$ $CHCl_3$ is accomplished by stirring the mixture at room temperature for several hours. In Step (c), the aldehyde, dissolved in an aromatic hydrocarbon solvent such as benzene or toluene, is reacted at 60° to 80° C. for several hours with diethyl phosphite in the presence of N,N-diisopropylethyl amine under an inert atmosphere. As indicated in Step (d), a six to twelve hour reflux of the triester in from 2 to 6N hydrochloric acid (HCl) provides the imidazo-pyridine phosphonic-carboxylic acid product. Alternatively, in Step (e), the imidazopyridine is oxidized with periodinane in a chlorocarbon solvent such as $CH_2Cl_2$ or $CHCl_3$ to the heterocyclic ketone. Step (g) illustrates a six to twelve hour reflux of the triester in from 2 to 6N HCl to generate the imidazo-pyridine phosphonic-carboxylic acid product. Alternatively, the benzylic alcohole of Step (f) is treated with an equivalent of diethylaminosulphur trifluoride (Dast) in a chlorocarbon solvent such as $CH_2Cl_2$ or $CHCl_3$ at ambient temperature under an inert atmosphere to yield the fluoro analog. The compound is subsequently converted in Step (i) to the fluoro imidazo-pyridine phosphonic carboxylic acid product.

The following Examples 1–95 are detailed descriptions of the methods of preparation of compounds of Formula I and Formula II. These detailed preparations fall within the scope of, and serve to exemplify, the above described Generic Procedures which form part of the invention. These Examples 1–95 are presented for illustrative purposes only and are not intended as a restriction on the scope of the invention. All parts are by weight unless otherwise indicated. Most of the commercially-available starting materials were obtained from Aldrich Chemical Co., Milwaukee, Wis.

EXAMPLE 1

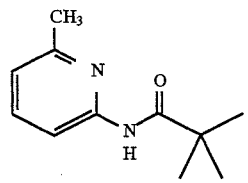

2,2-dimethyl-N-(6-methyl-2-pyridinyl)propanamide

A 3-L flask equipped with a nitrogen ($N_2$) inlet, thermometer and addition funnel was charged with dichloromethane ($CH_2Cl_2$, 1400 mL) and 2-amino-6-methylpyridine (130 g, 1.2 mol, Aldrich). After cooling the reaction to 0° C. in a wet ice/water bath, triethylamine ($Et_3N$, 151.5 g, 1.5 mol) was added. Trimethylacetyl chloride (159.15 g, 1.32 mol) was diluted with $CH_2Cl_2$ (100 mL) and added dropwise to the reaction over 1.5 h. The reaction was stirred for an additional 30 min at room temperature. The salts were filtered from the reaction and the filtrate was washed twice with $H_2O$. Drying the filtrate with anhydrous magnesium sulfate ($MgSO_4$) and stripping all solvent in vacuo left a yellowish colored solid. Recrystallization from diethyl ether ($Et_2O$)/hexanes (Hex) provided 167.3 g (73%) of pure product. The identity of this material and that of subsequent examples were confirmed by NMR (300 MHz), microanalysis, and infrared spectroscopy, unless otherwise noted.

EXAMPLE 2

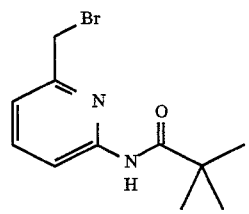

N-[6-bromomethyl)-2-pyridinyl]-2,2-dimethylpropanamide

Carbon tetrachloride ($CCl_4$, 300 mL) and the product from Example 1 (50.6 g, 0.26 mol) were placed in a 1-L flask equipped with a $N_2$ inlet. The solution was stirred until all solid dissolved. N-bromosuccinimide (NBS, 46.8 g, 0.26 mol) was then added to the reaction flask, followed by 2,2'-azobisisobutyronitrile (AIBN, 0.02 g). The reaction was heated to reflux for 7 h with a 500 watt reflector spot lamp. After cooling the reaction to room temperature, it was filtered and all solvent was removed under reduced pressure. Flash chromatography (15/85 ethyl acetate (EtOAc)/Hex) provided 24.89 g (37%) of title product.

EXAMPLE 3

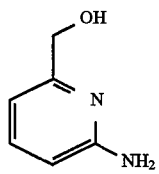

6-amino-2-pyridinemethanol

The product of Example 2 (24.89 g, 96 mmol) and 10%(v/v) $H_2SO_4$ (100 mL) were combined in a 250 mL flask. The reaction was heated to reflux for 8 h and then cooled to room temperature. The reaction was made basic with aq $K_2CO_3$ and extracted with EtOAc. The extracts were dried ($MgSO_4$), decolorized with activated charcoal, and filtered. Removal of all solvent in vacuo gave 8.49 g (71%) of the desired product.

EXAMPLE 4

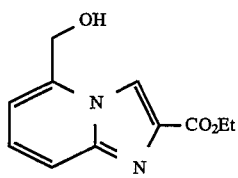

ethyl 5-(hydroxymethyl)imidazo[1,2-a]pyridine-2-carboxylate (HCl)

To a 100 mL flask under a $N_2$ atmosphere were added ethylene glycol dimethyl ether (DME, 120 mL) and the product of Example 3 (8.49 g, 68 mmol). After stirring for 20 min, ethyl bromopyruvate (13.5 g, 69 mmol) was added and the reaction allowed to stir at room temperature for 16 h. The resulting precipitate was filtered and washed once with $Et_2O$. The solid was then suspended in absolute ethanol (abs EtOH, 35 mL) and heated to reflux for 4 h. The resulting solution was cooled to room temperature and all solvent removed in vacuo. Aqueous $K_2CO_3$ was added to the residue, and the product was extracted with $CH_2Cl_2$. The extracts were dried ($MgSO_4$), treated with activated charcoal, filtered, and stripped to leave 9.09 g (60%) of the title compound.

EXAMPLE 5

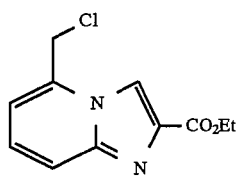

ethyl 5-(chloromethyl)imidazo[1,2-a]pyridine-2-carboxylate

To a 250 mL flask containing chloroform ($CHCl_3$, 100 mL) was added the product from Example 4 (4.65 g, 21 mmol), followed by the slow addition of thionylchloride ($SOCl_2$, 2.97 g, 25 mmol). After stirring 3 h, the solvent was removed in vacuo. Aqueous $K_2CO_3$ was added to the residue and the product extracted with EtOAc. After the extracts were dried ($MgSO_4$), all solvent was removed under reduced pressure to give 4.9 g (97%) of pure product.

EXAMPLE 6

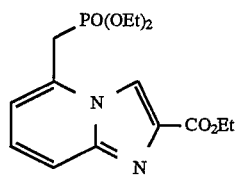

ethyl 5-[(diethoxyphosphinyl)methyl]imidazo[1,2-a]pyridine-2-carboxylate

In a 250 mL flask equipped with $N_2$ inlet, condensor, and stopper were combined the product from Example 5 (4.9 g, 20 mmol) and methyl ethyl ketone (MEK, 100 mL). Sodium iodide (NaI, 3 g, 20 mmol) was added to the reaction, which was allowed to stir at room temperature for 30 min. Triethyl phosphite (3.66 g, 22 mmol) was added and the reaction was heated to reflux for 4.5 h. After cooling to room temperature, aq $K_2CO_3$ was added, and the product was extracted with EtOAc. The extracts were dried ($MgSO_4$), decolorized with activated charcoal, filtered and stripped of all solvent to give the crude yellow product. Flash chromatography (96/4 EtOAc/EtOH) provided 2.65 g (39%) of clean title product.

Analysis Calcd. for $C_{15}H_{21}N_2O_5P$ (MW=340.32) C, 52.94; H, 6.22; N, 8.23. Found C, 52.82; H, 6.51; N, 8.05.

EXAMPLE 7

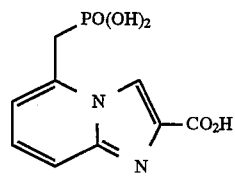

5-(phosphonomethyl)imidazo[1,2-a]pyridine-2-carboxylic acid (HCl)

A 50 mL flask was charged with the product from Example 6 (2.0 g, 6 mmol) and 4N. HCl (25 mL). The reaction was heated to reflux for 12 h. After cooling to room temperature, the solvent was removed in vacuo. Trituration of the residue with $Et_2O$, and filtration of the title product yielded 1.0 g of product HCl salt after oven drying.

Analysis Calcd. for $C_9H_9N_2O_5P+1.25$ HCl+1.25 $H_2O$ (MW=324.25) C, 33.34; H, 3.96; N, 8.64. Found C, 33.71; H, 3.78; N, 8.55.

EXAMPLE 8

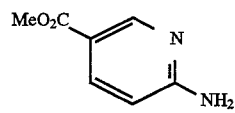

methyl 6-amino-3-pyridinecarboxylate

To a 25 mL flask under a $N_2$ atmosphere was added methanol (MeOH, 15 mL) and 6-aminonicotinic acid (1.0 g, 7.2 mmol). The resulting suspension was cooled to 0° C. in a wet ice/water bath. Thionylchloride (1.69 g, 14.4 mmol) was then added dropwise and the solution allowed to warm to room temperature over 16 h. Additional $SOCl_2$ (1.63 g, 13.7 mmol) was added and the reaction heated to reflux for 7 h. The reaction was cooled to room temperature and evaporation of all solvent produced the title HCl salt.

EXAMPLE 9

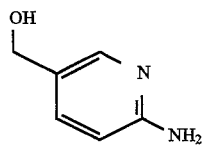

6-amino-3-pyridinemethanol

A 250 mL 3-neck flask equipped with an addition funnel, an argon (Ar) inlet and a stopper was flame dried and cooled to room temperature. Dry tetrahydrofuran (THF, 30 mL) was added to the flask, followed by 1M. lithium aluminum hydride (LAH) in Et$_2$O (16 mL). After cooling the solution to 0° C. with a wet ice/water bath, the product from Example 8 (0.92 g, 6 mmol) suspended in TEF (100 mL) was added dropwise. The reaction was allowed to warm to room temperature and stir for 3 h. The reaction was quenched with H$_2$O, the salts filtered off and the filtrate stripped to give 0.591 g (99%) of title material.

EXAMPLE 10

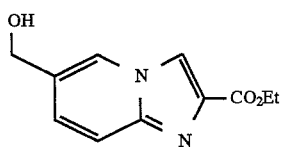

ethyl 6-(hydroxymethyl)imidazo[1,2-a]pyridine-2-carboxylate

To a 100 mL flask under a N$_2$ atmosphere were added DME (35 mL) and the product from Example 9 (0.60 g, 4.8 mmol). After stirring for 20 min, ethyl bromopyruvate (1.03 g, 5.3 mmol) was added and the reaction was allowed to stir at room temperature for 16 h. The resulting precipitate was filtered and washed once with Et$_2$O. The solid was suspended in abs EtOH (35 mL) and heated to reflux for 2 h. The resulting solution was cooled to room temperature and all solvent removed in vacuo. Aqueous K$_2$CO$_3$ was added to the residue, and the product was extracted with CH$_2$Cl$_2$. The extracts were dried (MgSO$_4$) and stripped to leave 0.793 g (75%) of title product.

EXAMPLE 11

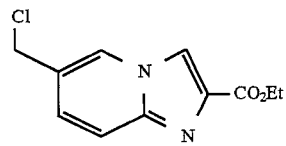

ethyl 6-(chloromethyl)imidazo[1,2-a]pyridine-2-carboxylate

By the method of Example 5, the product from Example 10 (2.52 g, 11.4 mmol) dissolved in CHCl$_3$ (100 mL) was reacted with SOCl$_2$ (1.5 g, 12.6 mmol). Final workup provided 2.66 g (98%) of title compound.

EXAMPLE 12

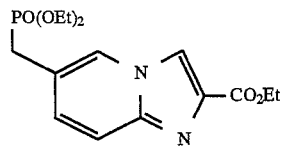

ethyl 6-[(diethoxyphosphinyl)methyl]imidazo[1,2-a]pyridine-2-carboxylate

By the method of Example 6, the product from Example 11 (2.66 g, 11.1 mmol) was treated with NaI (1.67 g, 11.1 mmol) and triethyl phosphite (2.03 g, 12.2 mmol). Workup produced 1.61 g (43%) of title compound.

EXAMPLE 13

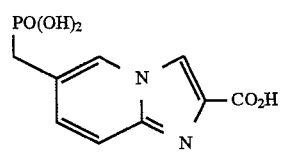

6-(phosphonomethyl)imidazo[1,2-a]pyridine-2-carboxylic acid (HCl)

By the procedure of Example 7, the product from Example 12 (0.21 g crude) was refluxed in 4N. HCl (16 mL) for 24 h. Workup produced 0.1 g of the title HCl salt.

Analysis Calcd. for C$_9$H$_9$N$_2$O$_5$P+1.1 HCl+0.5 H$_2$O (MW=305.26) C, 35.41 H, 3.67; N, 9.18. Found C, 35.39; H, 3.58 N, 9.36.

EXAMPLE 14

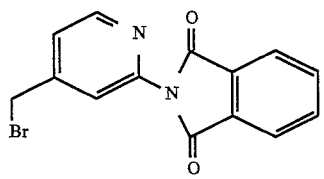

2-[4-(bromomethyl)-2-pyridinyl]-1H-isoindole-1,3(2H)-dione

Following the procedure of Example 32, equimolar amounts of 2-aminopicoline and phthalic anhydride were reacted to give 2-(4-methyl-2-pyridinyl)-1H-isoindole-1,3 (2H)-dione. This product (1.0 g, 4.2 mmol) was then reacted with NBS (0.747 g, 4.2 mmol) in CH$_2$Cl$_2$ (50 mL), using the procedure of Example 2, to give the title compound.

EXAMPLE 15

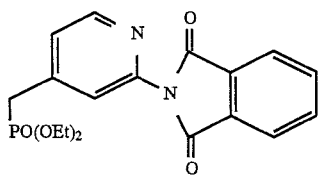

diethyl [[2-(1,3-dihydro-1,3-dioxo-2H-isoindol-2-yl)-4-(pyridinyl)methyl]phosphonate The product from Example 14, triethyl phosphite (7.66 g, 46 mmol) and a catalytic amount of potassium iodide were placed in a flask containing MEK (500 mL) under a $N_2$ atmosphere. The reaction was heated to reflux for 11 h. After cooling to room temperature, the solid was filtered from the reaction mixture, and the filtrate stripped in vacuo. Aqueous $K_2CO_3$ was added to the residue, and the product extracted with EtOAc. The extract was dried ($MgSO_4$), filtered and stripped of all solvent in vacuo to produce the crude product which was purified by flash chromatography (97/3 $CHCl_3$/EtOH).

EXAMPLE 16

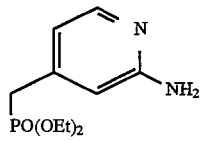

diethyl [(2-amino-4-pyridinyl)methyl]phosphonate

The product from Example 15 (1.4 g, 3.7 mmol) was dissolved in $CH_2Cl_2$ (10 mL) and placed in a 25 mL flask. Hydrazine monohydrate (0.187 g, 3.7 mmol) was added to the flask, and the reaction was allowed to stir at room temperature for 2 h. Two additional equivalents of hydrazine monohydrate were added to drive the reaction to completion. Filtering and solvent removal under reduced pressure gave 0.87 g of crude title compound which was used without further purification.

EXAMPLE 17

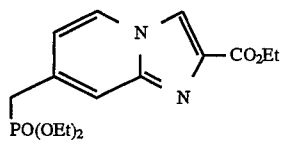

ethyl 7-[(diethoxyphosphinyl)methyl]imidazo[1,2-a]-pyridine-2-carboxylate

The product from Example 16 (0.87 g, 3.56 mmol) was dissolved in DME (25 mL) and placed in a 100 mL flask. Ethyl bromopyruvate (0.76 g, 3.92 mmol) was added to the flask, and the reaction was allowed to stir under a $N_2$ atmosphere for 16 h. After solvent removal in vacuo, the residue was taken up in abs EtOH (25 mL) and refluxed for 5 h. The reaction was cooled to room temperature and solvent was removed in vacuo. The residue was dissolved in aqueous $K_2CO_3$ and the product extracted with EtOAc. Purification via a chromatotron (97/2/1 $CH_2Cl_2$/EtOH/$NH_4OH$) produced 0.38 g (32%) of title compound.

Analysis Calcd. for $C_{15}H_{21}N_2O_5P$ (MW=340.31) C, 52.94; H, 6.22; N, 8.23 Found C, 52.65; H, 6.20; N, 8.05.

EXAMPLE 18

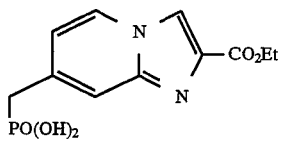

7-(phosphonomethyl)imidazo[1,2-a]pyridine-2-carboxylic acid (HCl)

Following the procedure of Example 7, the product from Example 17 (0.32 g, 0.9 mmol) was dissolved in 4N. HCl (25 mL). Final purification provided the title compound as the HCl salt.

Analysis Calcd. for $C_9H_9N_2O_5P+0.9$ HCl+0.5 $H_2O$ (MW=297.97) C, 36.28; H, 3.69; N, 9.40. Found C, 36.31; H, 3.63; N, 9.18.

EXAMPLE 19

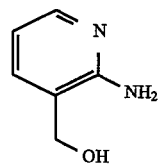

2-amino-3-(hydroxymethy)pyridine

This compound was synthesized referencing the method of Murakami, et.al., Bull. Chem. Soc. Jap. 1973, 46(7), 2187.

EXAMPLE 20

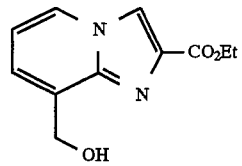

ethyl 8-(hydroxymethyl)imidazo[1,2-a]pyridine-2-carboxylate

Following the procedure of Example 10, the product from Example 19 (5.0 g, 40 mmol) was combined with ethyl bromopyruvate (8.58 g, 44 mmol) in DME (50 mL). Final product purification gave 5.24 g (60%) of title compound.

EXAMPLE 21

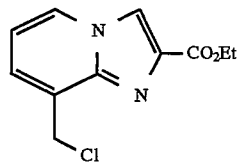

ethyl 8-(chloromethyl)imidazo[1,2-a]pyridine-2-carboxylate

The product from Example 20 (5.0 g, 23 mmol) was dissolved in $CHCl_3$ (50 mL) and placed in a 100 mL flask. Thionylchloride (2.97 g, 25 mmol) was added dropwise to the reaction. The reaction was heated to reflux for 1 h. After cooling the reaction to room temperature, aq $KHCO_3$ was added to the solution, and product was extracted with $CHCl_3$. The organic extracts were dried ($MgSO_4$), treated with activated charcoal, filtered and stripped in vacuo to leave the title compound as a tan solid (4.97 g, 91%).

EXAMPLE 22

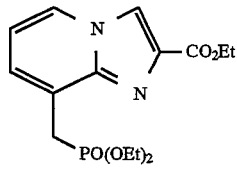

ethyl 8-[(diethoxyphosphinyl)methyl]imidazo[1,2-a]-pyridine-2-carboxylate

By the method of Example 6, the product from Example 21 was dissolved in MEK (130 mL) and treated with NaI (3.4 g, 23 mmol) and triethyl phosphite (5.32 g, 32 mmol). Final purification via flash chromatography (95/4.5/0.5 EtOAc/EtOH/Et₃N) provided 3.23 g (45%) of title compound.

EXAMPLE 23

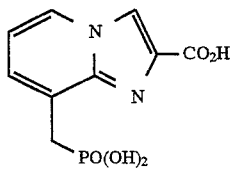

8-(phosphonomethyl)imidazo[1,2-a]pyridine-2-carboxylic acid (HCl)

Following the procedure for Example 7, the product from Example 22 (3.23 g, 9.5 mmol) was combined with 4N. HCl (15 mL) to give 2.64 g of title compound as the HCl salt.

Analysis Calcd. for $C_9H_9N_2O_5P+1.0$ HCl+1.5 $H_2O$ (MW=319.64) C, 33.81; H, 4.10; N, 8.76. Found C, 33.47; H, 4.03; N, 8.62.

EXAMPLE 24

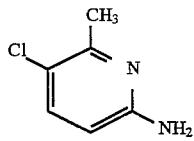

5-chloro-6-methyl-2-pyridinamine

This compound was prepared according to the procedure of Kress, et.al., J. Org. Chem., 1976, (41), 93.

EXAMPLE 25

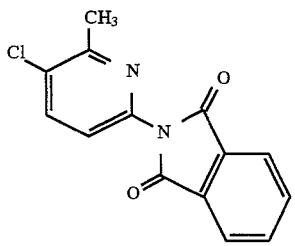

2-(5-chloro-6-methyl-2-pyridinyl)-1H-isoindole-1,3(2H)-dione

By the method of Example 32, the product from Example 24 (5.0 g, 35 mmol) was reacted with phthalic anhydride (5.19 g, 35 mmol). Final workup produced 8.18 g (86%) of the title compound.

EXAMPLE 26

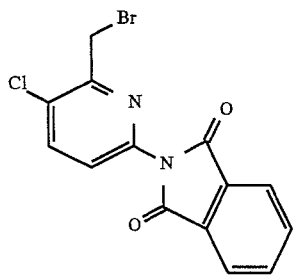

2-[6-(bromomethyl)-5-chloro-2-pyridinyl]-1H-isoindole-1,3(2H)-dione

Following the procedure of Example 2, the product from Example 25 (6.07 g, 22 mmol) was reacted with NBS (3.96 g, 22 mmol) in $CH_2Cl_2$ (150 mL). The crude title product (8.98 g, >100%) was obtained and used without further purification.

EXAMPLE 27

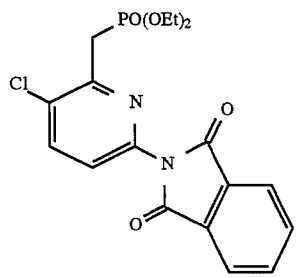

diethyl [[3-chloro-6-(1,3-dihydro-1,3-dioxo-2H-isoindol-2-yl)-2-pyridinyl]methyl]phosphonate The product from Example 26 was dissolved in MEK (180 mL) and placed in a 500 mL flask under a $N_2$ atmosphere. Sodium iodide (catalytic) was added to the reaction which was subsequently stirred at room temperature for 20 min. Triethyl phosphite (3.66 g, 22 mmol) was added to the reaction. The reaction was heated to reflux for 6 h, cooled to room temperature, and stirred an additional 16 h. The reaction was filtered and all solvent removed in vacuo to yield the crude title compound. Purification via flash chromatography (96/4 $CHCl_3$/EtOH) produced the pure title product.

EXAMPLE 28

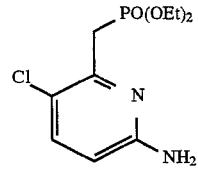

diethyl [(6-amino-3-chloro-2-pyridinyl)methyl]phosphonate

Following the procedure from Example 16, the product from Example 27 (1.0 g, 2.4 mmol) was reacted with hydrazine monohydrate (0.121 g, 2.4 mmol) in $CH_2Cl_2$ (25 mL). Workup produced the crude title product which was used without further purification.

EXAMPLE 29

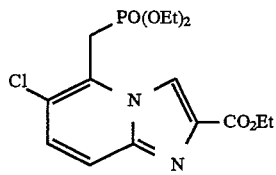

ethyl 6-chloro-5-[(diethoxyphosphinyl)methyl]-
imidazo[1,2-a]pyridine-2-carboxylate Following the procedure for Example 17, the residue from Example 28 was combined with ethyl bromopyruvate (0.468 g, 2.4 mmol) in DME (25 mL). After the resulting salt was refluxed in abs EtOH (30 mL) for 6 h, workup and puricication produced 0.114 g (13%) of title compound.

Analysis Calcd. for $C_{15}H_{20}N_2O_5PCl$ (MW=374.76) C, 48.07; H, 5.38; N, 7.47. Found C, 47.82; H, 5.30; N, 7.41.

EXAMPLE 30

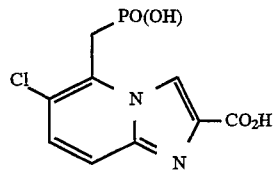

6-chloro-5-(phosphonomethyl)imidazo[1,2-a]pyridine-
2-carboxylic acid

Following the procedure in Example 7, the product from Example 29 was refluxed in 4N. HCl (7 mL) for 7 h. Workup produced the title product HCl salt.

Analysis Calcd. for $C_9H_8N_2O_5PCl+1.0$ $H_2O$ (MW=308.62) C, 35.03; H, 3.27; N, 9.08. Found C, 34.93; H, 3.36; N, 8.93.

EXAMPLE 31

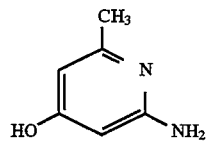

4-hydroxy-6-methyl-2-pyridinamine

Concentrated ammonium hydroxide (NH$_4$OH, 1.2 L) and 4-hydroxy-6-methyl-2-pyrone (148 g, 1.17 mol) were combined in a Parr bomb. The bomb was shaken and heated to 200° C. for 20 h. After cooling the bomb to room temperature, the heterogeneous reaction mixture was filtered. The solid product residue was washed with water and Et$_2$O before it was dissolved in boiling MEOW, decolorized with activated charcoal, and crystallized. Three crops of analytically pure title compound were obtained (84.3 g, 57.8%).

Analysis Calcd for $C_6H_8N_2O$ (MW=124.14) C, 58.05; H, 6.50; N, 22.57. Found C, 57.72; H, 6.63; N, 22.63.

EXAMPLE 32

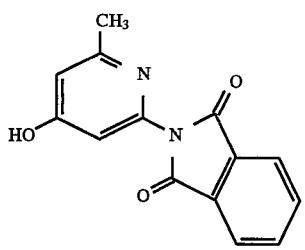

2-(4-hydroxy-6-methyl-2-pyridinyl)-1H-isoindole-
1,3(2H)-dione

The title compound from Example 31 (2.5 g, 20.0 mmol) and phthalic anhydride (3.0 g, 20.0 mmol) were ground in a mortor. This mixture was added to a flask which was flushed with N$_2$ and immersed in an oil bath maintained at 190° C. Heating was continued for 2 h while a gentle flow of N$_2$ was passed through the flask to removed the water by-product. The reaction was cooled to room temperature and the product solid was filtered and washed extensively with 100 mL aliquotes of CH$_2$Cl$_2$, MeOH, EtOAc, and Et$_2$O. After drying, 4.63 g (92%) of the title material was obtained.

Analysis Calcd. for $C_{14}H_{10}N_2O_3$ (MW=254.25) C, 66.14; H, 3.96; N, 11.02. Found C, 65.81; H, 4.02; N, 10.95.

EXAMPLE 33

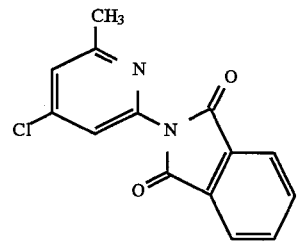

2-(4-chloro-6-methyl-2-pyridinyl)-1H-isoindole-
1,3(2H)-dione

The title compound from Example 32 is heated at 200° C. with excess phosphorusoxychloride (POCl$_3$) under an Ar atmosphere. The reaction mixture is poured into ice water and this solution is extracted with Et$_2$O. After washing with saturated potassium carbonate (K$_2$CO$_3$), the solution is dried and stripped of all solvent to give the desired compound.

EXAMPLE 34

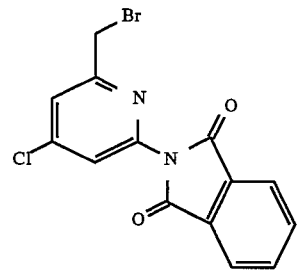

2-[6-(bromomethyl)-4-chloro-2-pyridinyl]-1H-
isoindole-1,3(2H)-dione

The title material is prepared from the title product of Example 33 by the method of Example 2.

EXAMPLE 35

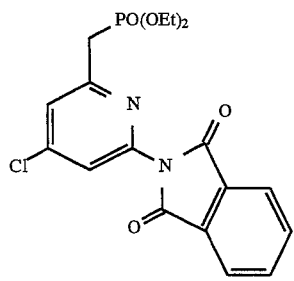

diethyl [[4-chloro-6-(1,3-dihydro-1,3-dioxo-2H-isoindol-2-yl)-2-pyridinyl]methyl]phosphonate The title material is synthesized from the title product of Example 34 by the method of Example 27.

EXAMPLE 36

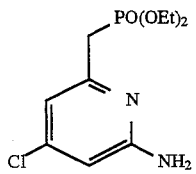

diethyl [(6-amino-4-chloro-2-pyridinyl)methyl]phosphonate

The title compound is prepared from the title product of Example 35 by the method of Example 16.

EXAMPLE 37

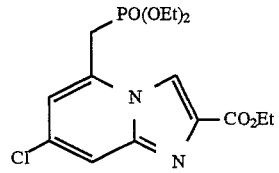

ethyl 7-chloro-5-[(diethoxyphosphinyl)methyl]imidazo[1,2-a]pyridine-2-carboxylate The title material is synthesized from the title product of Example 36 by the method of Example 17.

EXAMPLE 38

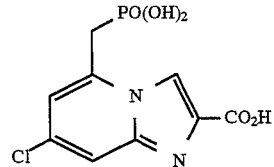

7-chloro-5-(phosphonomethyl)imidazo[1,2-a]pyridine-2-carboxylic acid

The title compound is prepared from the title product of Example 37 by the method of Example 7.

EXAMPLE 39

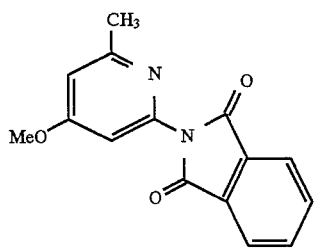

2-(4-methoxy-6-methyl-2-pyridinyl)-1H-isoindole-1,3(2H)-dione

The title material from Example 32 (4.32 g, 17.1 mmol) was combined with $K_2CO_3$ (2.37 g, 17.1 mmol), methyl iodide (2.4 g, 17.1 mmol), and 40 mL of acetone. This heterogeneous mix was stirred at room temperature for two weeks before it was suction filtered and the solid washed with water and $Et_2O$. The residue white solid is the desired title product.

EXAMPLE 40

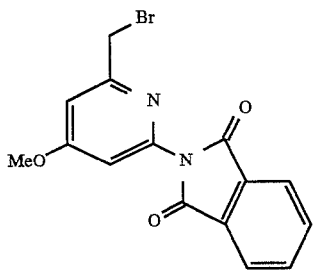

2-[6-(bromomethyl)-4-methoxy-2-pyridinyl]-1H-isoindole-1,3(2H)-dione

The title compound is prepared from the title product of Example 39 by the method of Example 2.

EXAMPLE 41

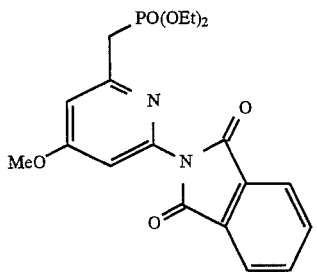

diethyl [[6-(1,3-dihydro-1,3-dioxo-2H-isoindol-2-yl)-4-methoxy-2-pyridinyl]methyl]phosphonate The title material is synthesized from the title product of Example 40 by the method of Example 27.

EXAMPLE 42

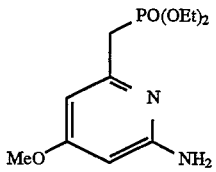

diethyl [(6-amino-4-methoxy-2-pyridinyl)methyl]phosphonate

The title compound is prepared from the title product of Example 41 by the method of Example 16.

EXAMPLE 43

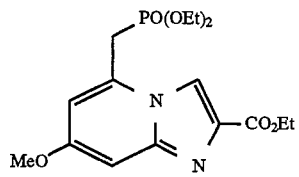

ethyl 5-[(diethoxyphosphinyl)methyl]-
7-methoxyimidazo[1,2-a]pyridine-2-carboxylate The title material is synthesized from the title product of Example 42 by the method of Example 17.

EXAMPLE 44

7-methoxy-5-(phosphonomethyl)imidazo[1,2-a]pyridine-2-carboxylic acid

The title material is prepared from the title product of Example 43 by the method of Example 7.

EXAMPLE 45

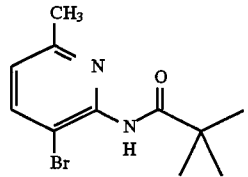

N-(3-bromo-6-methyl-2-pyridinyl)-2,2-dimethylpropanamide

Carbontetrachloride ($CCl_4$, 300 mL) and the product of Example 1 (50.6 g, 0.26 mol) were added to a 1 L flask equipped with a $N_2$ inlet The solution was stirred until all solid dissolved. N-bromosuccinimide (NBS, 46.8 g, 0.26 mol) was then added to the reaction flask, followed by 2,2'-azobisisobutyronitrile (AIBN, 0.02 g). The reaction was heated to reflux for 6 h with a 500 watt reflector spot lamp. An additional 0.5 eq (23.4 g) of NBS was added to the reaction, and refluxing was continued for 2 h. After cooling the reaction to room temperature, it was filtered and all solvent was removed under reduced pressure. Flash chromatography (15/85 EtOAc/Hex) provided 31.6 g (47%) of title product and 22.2 g (33%) of the title material of Example 2.

EXAMPLE 46

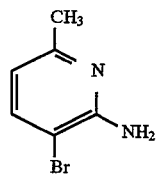

3-bromo-6-methyl-2-pyridinamine

Following the procedure from Example 3, the product from Example 45 (26.1 g, 96 mmol) was refluxed in 10% (v/v) $H_2SO_4$ (200 mL) to produce 11.14 g (62%) of title compound.

EXAMPLE 47

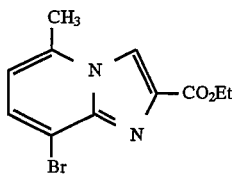

ethyl 8-bromo-5-methylimidazo*1,2-a*pyridine-2-carboxylate

Following the procedure for Example 6, the product from Example 46 (11.14 g, 60 mmol) was reacted with ethyl bromopyruvate (11.7 g, 60 mmol) in DME (100 mL). After the isolated salt was refluxed in abs EtOH (100 mL) for 2 h, 6.9 g (41%) of the title product was obtained.

Analysis Calcd. for $C_{11}H_{11}N_2O_2Br$ (MW=283.13) C, 46.67; H, 3.92; N, 9.89. Found C, 46.39; H, 3.88; N, 9.82.

EXAMPLE 48

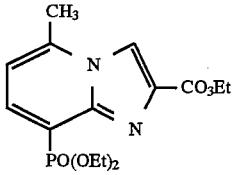

ethyl 8-(diethoxyphosphinyl)-5-methylimidazo[1,2-a]-
pyridine-2-carboxylate

Toluene (10 mL) was placed in a 25 mL 3-neck flask equipped with a condensor, Ar inlet and stopper. The product from Example 47 (0.736 g, 2.6 mmol), diethylphosphite (1.1 g, 7.8 mmol) and $Et_3N$ (0.8 g, 7.8 mmol) were placed in the flask, which was then heated to 80° C. Tetrakis (triphenylphosphine) Palladium(0) [Pd (0), 0.4 g, 0.35 mmol] was added to the reaction and heating was continued for 22 h at which point an additional 0.12 g of Pd(0) was added to the reaction. Heating was continued for an additional 7 h. The reaction was cooled to room temperature and stirred 50 h. Diethyl ether was added to the reaction to dissolve the salts which had formed. Purification via a chromatotron (97/2.5/0.5 $CH_2Cl_2$/EtOH/$NH_4OH$) provided 0.06 g (7%) of title product.

EXAMPLE 49

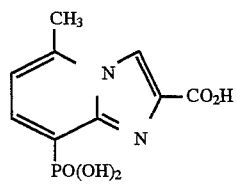

5-methyl-8-phosphonoimidazo[1,2-a]pyridine-2-carboxylic acid

The title material is prepared from the product of Example 48 by the method of Example 7.

EXAMPLE 50

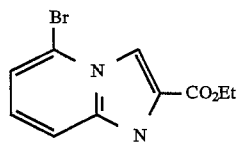

ethyl 5-bromoimidazo[1,2-2]pyridine-2-carboxylate

Ethylene glycol dimethylether (DME, 80 mL) and 2-bromo-5-aminopyridine (5 g, 28.9 mmol) were combined in a flask under $N_2$. After stirring this mixture for 20 min, ethyl bromopyruvate (6.75 g, 34.6 mmol) was added and the reaction was allowed to stir at room temperature for 16 h. The reaction was completed following the procedure of Example 4 to give 6.4 g (82%) of the title product.

Analysis Calcd. for $C_{10}H_9N_2O_2Br$ (MW=269.10) C, 44.63; H, 3.37; N, 10.41; Br, 29.69. Found C, 44.38; H, 3.34; N, 10.54; Br, 28.39.

EXAMPLE 51

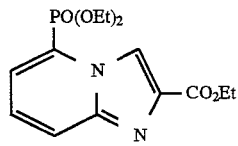

ethyl 5-(diethoxyphosphinyl)imidazo[1,2-a]pyridine-2-carboxylate

The product from Example 50 (4.0 g, 14.9 mmol), diethylphosphite (6.28 g, 45.5 mmol) $Et_3N$ (4.51 g, 45.5 mmol) and toluene (20 mL) were combined in a flask equipped with a $N_2$ inlet, condensor and stopper. After heating this mixture to 75° C., tetrakis(triphenylphosphine) Palladium(0) [2.3 g, 2.0 mmol] was added and the reaction was heated at 90° C. for 2 h. The reaction was cooled to room temperature, diluted with $Et_2O$, and filtered. The filtrate was concentrated and 2.1 g (39%) of the title product was isolated by high performance liquid chromatography (HPLC).

EXAMPLE 52

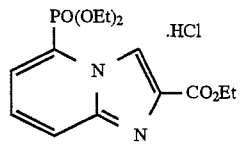

ethyl 5-(diethoxyphosphinyl)imidazo[1,2-a]pyridine-2-carboxylate, monohydrochloride The product from Example 51 (1.6 g, 4.4 mmol) was dissolved in $CH_2Cl_2$ (30 mL), treated with activated charcoal and filtered. To this filtrate was then added 6N HCl in dioxane (0.9 mL, 4.4 mmol) followed by $Et_2O$ (100 mL). The precipitated product was filtered, washed with $Et_2O$, and dried in vacuo.

Analysis Calcd. for $C_{14}H_{19}N_2O_5P+0.9$ HCl+1 $H_2O$ (MW=377.12) C, 44.59; H, 5.85; N, 7.43. Found C, 44.44; H, 5.46; N, 7.96.

EXAMPLE 53

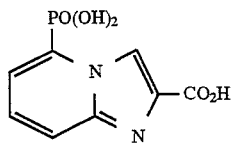

5-phosphonoimidazo[1,2-a]pyridine-2-carboxylic acid

The title material is synthesized from the title product of Example 52 by the method of Example 7.

EXAMPLE 54

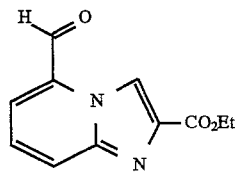

ethyl 5-formylimidazo[1,2-a]pyridine-2-carboxylate

Pyridinium chlorochromate (7.3 g, 33.8 mmol, Aldrich) and $CH_2Cl_2$ (100 mL) were added to a 300 mL beaker. This mixture was stirred until all solid had dissolved. The product from Example 4 (5.0 g, 22.7 mmol) was then added to the beaker and the mixture was stirred at room temperature for 2 h. Another 100 mL of $CH_2Cl_2$ was added before this mixture was filtered. The gummy residue was washed extensively until it became a solid. The combined filtrate was stripped of all solvent and the residue was flash chromatographed (10/89.2/0.2 acetone/$CH_2Cl_2$/$Et_3N$) to provide 3.3 g (67%) of the title material.

EXAMPLE 55

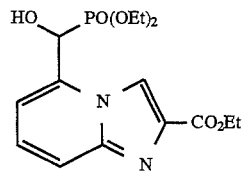

ethyl 5-[(diethoxyphosphinyl)hydroxymethyl]imidazo [1,2-a]pyridine-2-carboxylate Diethyl phosphite (1.7 g, 12.3 mmol, Aldrich), N,N-diisopropylethylamine (1.63 g, 12.4 mmol, Aldrich) and toluene (60 mL) were combined in a 100 mL flask equipped with a $N_2$ inlet and condensor. After warming this solution to 60° C., the product from Example 54 was added. After stirring at 75°–80° C. for 3 h, all solvent was removed from this mixture and the residue was chromatographed (7.5/92.4/0.1 isopropanol/$CH_2Cl_2$/HOAc) to give 1.2 g (66%) of the title product.

EXAMPLE 56

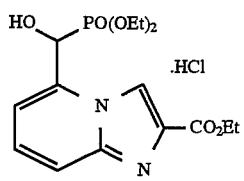

ethyl 5-[(diethoxyphosphinyl)hydroxymethyl]imidazo[1,2-a]pyridine-2-carboxylate, monohydrochloride The product from Example 55 (1.2 g, 3.37 mmol) was dissolved in $CH_2Cl_2$ (15 mL) and treated with 6N HCl in dioxane (0.56 mL, 3.37 mmol). The resulting salt was precipitated with $Et_2O$, filtered, washed with $Et_2O$, and dried in vacuo to give 1.3 g (99%) of the title product.

Analysis Calcd. for $C_{15}H_{21}N_2O_6P+HCl+0.25\ H_2O$ (MW=397.28) C, 45.35; H, 5.58; N, 7.05, Cl, 8.92. Found C, 45.38; H, 5.58; N, 6.94; Cl, 9.03.

EXAMPLE 57

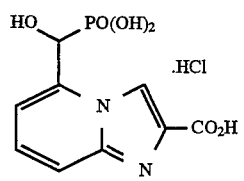

5-(hydroxyphosphonomethyl)imidazo[1,2-a]pyridine-2-carboxylic acid, monohydrochloride The title compound was synthesized from the title material of Example 56 (0.2 g, 0.5 mmol) and 50 mL of 4N HCl by the procedure of Example 7. A 50 mg sample of the product salt was obtained.

Analysis Calcd. for $C_9H_9N_2O_6P+HCl$ (MW=308.61) C, 35.03; H, 3.27; N, 9.08, Cl, 11.49. Found C, 35.07; H, 3.63; N, 8.57; Cl, 11.41.

EXAMPLE 58

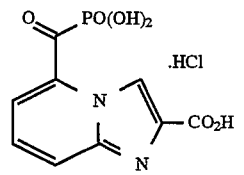

5-(phosphonocarbonyl)imidazo[1,2-a]pyridine-2-carboxylic acid, monohydrochloride The title material is prepared by oxidizing the product of Example 57 with periodinane in $CH_2Cl_2$.

EXAMPLE 59

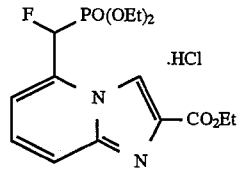

ethyl 5-[(diethoxyphosphinyl)fluoromethyl]imidazo-[1,2-a]pyridine-2-carboxylate, monohydrochloride The title material is synthesized by the reaction of the title product of Example 55 with diethylaminosulphur trifluoride (DAST) in $CH_2Cl_2$ using the method of Blackburn, G. M.; Kent, D. E. J. Chem. Soc., Chem. Comm. 1981, 511–513.

EXAMPLE 60

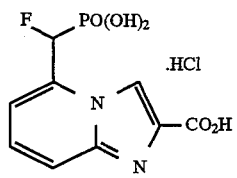

5-(fluorophosphonomethyl)imidazo[1,2-a]pyridine-2-carboxylic acid, monohydrochloride The title product is obtained from the title material of Example 59 by the method of Example 7.

EXAMPLE 61

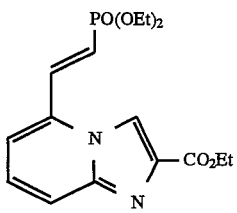

ethyl 5-[2-(diethoxyphosphinyl)-E-ethenyl]imidazo-[1,2-a]pyridine-2-carboxylate

Tetraethyl methylenediphosphonate (Lancaster) in benzene is added to a benzene solution of sodium hydride (NaH). The product from Example 54, also dissolved in benzene, is then added dropwise to the reaction mixture and stirred at room temperature under an Ar atmosphere. After stirring the resulting mixture for 2 h, it is diluted with $CHCl_3/H_2O$ (2/1). The $CHCl_3$ layer is separated and the aqueous layer is extracted with $CHCl_3$. Chromatography of the residue after removal of all solvent from the combined extracts gives the title product.

EXAMPLE 62

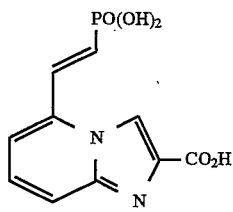

5-(2-phosphono-E-ethenyl)imidazo[1,2-a]pyridine-2-carboxylic acid

The title material is synthesized from the title product of Example 61 by the method of Example 7.

EXAMPLE 63

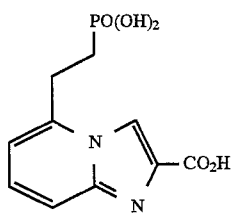

5-(2-phosphonoethyl)imidazo[1,2-a]pyridine-2-carboxylic acid

The title material is prepared by catalytic (Pd/C) hydrogenation of the title product of Example 62 under standard Parr conditions.

EXAMPLE 64

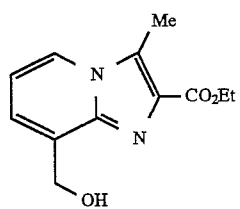

ethyl 8-(hydroxymethyl)-3-methylimidazo[1,2-a]pyridine-2-carboxylate

The title compound was synthesized by the method of Example 4. The product from Example 19 (2.0 g, 16 mmol) was reacted with 3-bromo-2-oxobutyric acid ethyl ester (3.7 g, 18 mmol) to give 2.85 g (76%) of title product.

EXAMPLE 65

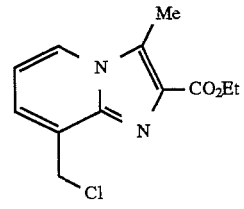

ethyl 8-(chloromethyl)-3-methylimidazo[1,2-a]pyridine-2-carboxylate

The title material was synthesized from the title product of Example 64 by the method of Example 5.

EXAMPLE 66

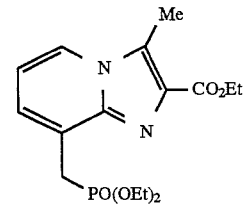

ethyl 8-[(diethoxyphosphinyl)methyl]-3-methylimidazo[1,2-a]pyridine-2-carboxylate The title material was synthesized from the title product of Example 65 by the method of Example 6.

Analysis Calcd. for $C_{16}H_{23}N_2O_5P$ (MW=354.34) C, 54.23; H, 6.54; N, 7.90. Found C, 53.92; H, 6.66; N, 7.77.

EXAMPLE 67

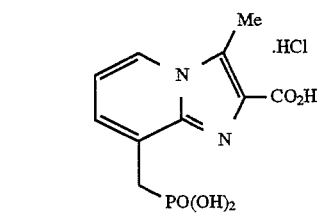

3-methyl-8-(phophonomethyl)imidazo[1,2-a]pyridine-2-carboxylic acid, monohydrochloride The title material was synthesized from the title product of Example 66 by the method of Example 7.

Analysis Calcd. for $C_{10}H_{11}N_2O_5P+0.8$ HCl+0.8 $H_2O$ (MW=313.76) C, 38.28; H, 4.30; N, 8.93. Found C, 38.39; H, 4.09; N, 9.06.

EXAMPLE 68

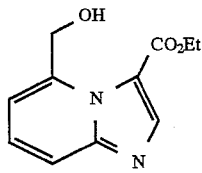

ethyl 5-(hydroxymethyl)imidazo[1,2-a]pyridine-3-carboxylate

The title product is prepared by the reaction of the title compound from Example 3 with ethyl a-chloroformylacetate by the method of Example 4 or in dioxane by the procedure of W. W. Paudley; R. A. VanDahm; Y. N. Park, J. Heterocyclic Chem., 1972, (9), 81–85.

EXAMPLE 69

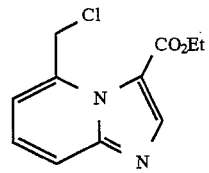

ethyl 5-(chloromethyl)imidazo[1,2-a]pyridine-3-carboxylate

The title material is synthesized from the title product of Example 68 by the method of Example 5.

EXAMPLE 70

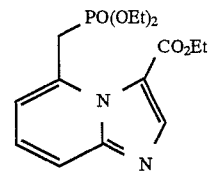

ethyl 5-[(diethyoxyphosphinyl)methyl]imidazo[1,2-a]pyridine-3-carboxylate

The title product is obtained from the title material of Example 69 by the method of Example 6.

EXAMPLE 71

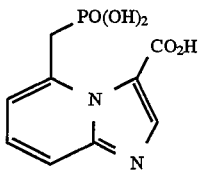

5-(phosphonomethyl)imidazo[1,2-a]pyridine-3-carboxylic acid

The title product is prepared from the title material of Example 70 by the method of Example 7.

EXAMPLE 72

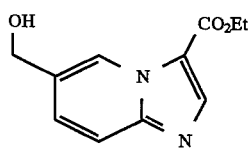

ethyl 6-(hydroxymethyl)imidazo[1,2-a]pyridine-3-carboxylate

The title material is synthesized from the title material of Example 9 by the methods suggested in Example 68.

EXAMPLE 73

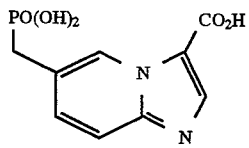

6-(phosphonomethyl)imidazo[1,2-a]pyridine-3-carboxylic acid

The title product is prepared from the title material of Example 72 by the successive application of the methods of Examples 5, 6, and 7.

EXAMPLE 74

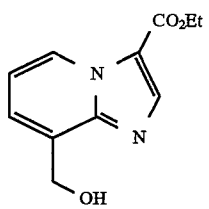

ethyl 8-(hydroxymethyl)imidazo[1,2-a]pyridine-3-carboxylate

The title product is prepared from the title material of Example 19 by the methods suggested in Example 68.

EXAMPLE 75

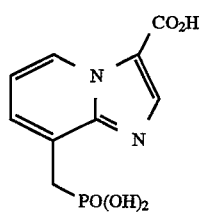

8-(phosphonomethyl)imidazo[1,2-a]pyridine-3-carboxylic acid

The title material is synthesized from the title material of Example 74 by the successive application of the methods of Examples 5, 6, and 7.

EXAMPLE 76

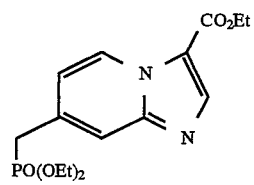

ethyl 7-[(diethoxyphosphinyl)methyl]imidazo[1,2-a]-pyridine-3-carboxylate

The title product is generated from the title material of Example 16 by the methods suggested in Example 68.

EXAMPLE 77

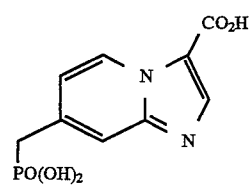

7-(phosphonomethyl)imidazo[1,2-a]pyridine-3-carboxylic acid

The title product is prepared from the title material of Example 76 by the method of Example 7.

EXAMPLE 78

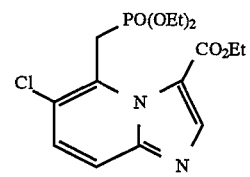

ethyl 6-chloro-5-[(diethoxyphosphinyl)methyl]imidazo-[1,2-a]pyridine-3-carboxylate The title product is obtained from the title material of Example 28 by the method of Example 17 or the procedures suggested in Example 68.

EXAMPLE 79

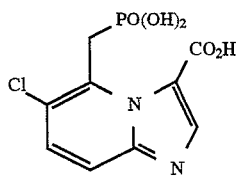

6-chloro-5-(phosphonomethyl)imidazo[1,2-a]pyridine-3-carboxylic acid

The title compound is prepared from the title material of Example 78 by the method of Example 7.

EXAMPLE 80

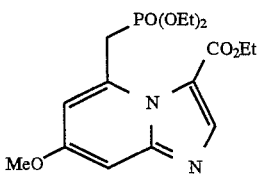

ethyl 5-[(diethoxyphosphinyl)methyl]-7-methoxy-imidazo[1,2-a]pyridine-3-carboxylate The title compound is synthesized from the title material of Example 42 by the method of Example 17 or the procedures suggested in Example 68.

EXAMPLE 81

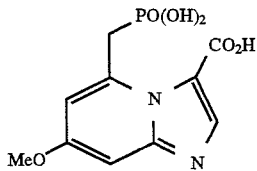

7-methoxy-5-(phosphonomethyl)imidazo[1,2-a]pyridine-3-carboxylic acid

The title compound is synthesized from the title material of Example 80 by the method of Example 7.

EXAMPLE 82

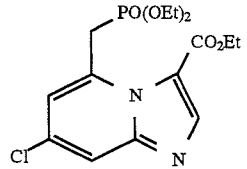

ethyl 7-chloro-5-[(diethoxyphosphinyl)methyl]imidazo-[1,2-a]pyridine-3-carboxylate The title material is synthesized from the title compound of Example 36 by the method of Example 17 or the procedures suggested in Example 68.

EXAMPLE 83

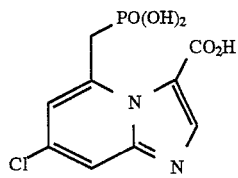

7-chloro-5-(phosphonomethyl)imidazo[1,2-a]pyridine-3-carboxylic acid

The title compound is prepared from the title material of Example 82 by the method of Example 7.

EXAMPLE 84

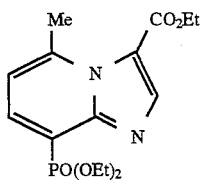

ethyl 8-(diethoxyphosphinyl)-5-methylimidazo[1,2-a]-pyridine-3-carboxylate

The title material is obtained from the title compound of Example 46 by successive application of the methods suggested in Example 68 and Example 48.

EXAMPLE 85

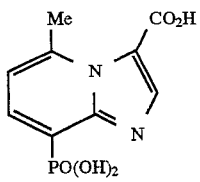

5-methyl-8-phosphonoimidazo[1,2-a]pyridine-3-carboxylic acid

The title product is synthesized from the title material of Example 84 by the method of Example 7.

EXAMPLE 86

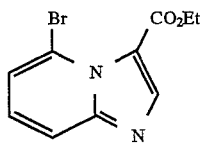

ethyl 5-bromoimidazo[1,2-a]pyridine-3-carboxylate

The title material is obtained from 2-bromo-5-aminopyridine by the method of Example 50 or the procedures suggested in Example 68.

EXAMPLE 87

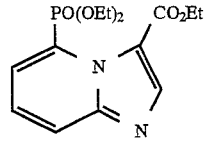

ethyl 5-(diethoxyphosphinyl)imidazol[1,2-a]pyridine-3-carboxylate

The title product is synthesized from the title material of Example 86 by the method of Example 51.

EXAMPLE 88

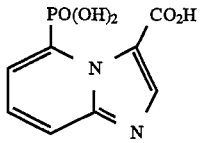

5-phophonoimidazo[1,2-a]pyridine-3-carboxylic acid

The title compound is prepared from the title material of Example 87 by the method of Example 7.

EXAMPLE 89

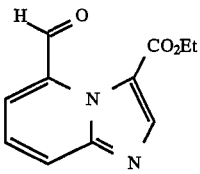

ethyl 5-formylimidazo[1,2-a]pyridine-3-carboxylate

The title material is synthesized from the title product of Example 68 by the method of Example 54.

EXAMPLE 90

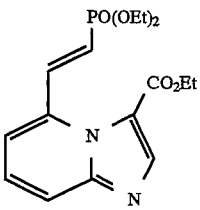

ethyl 5-[2-(diethyoxyphosphinyl)-E-ethenyl]imidazo [1,2-a]pyridine-3-carboxylate The title compound is prepared from the title material of Example 89 by the method of Example 61.

EXAMPLE 91

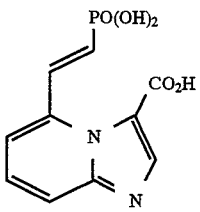

5-(2-phosphono-E-ethenyl)imidazo[1,2-a]pyridine-3-carboxylic acid

The title material is prepared from the title product of Example 90 by the method of Example 7.

EXAMPLE 92

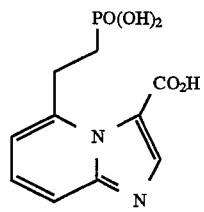

5-(2-phosphonoethyl)imidazo[1,2-a]pyridine-3-carboxylic acid

The title compound is generated from the title material of Example 91 by the method of Example 63.

EXAMPLE 93

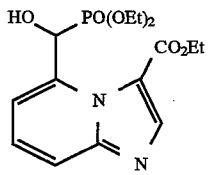

ethyl 5-[(diethoxyphosphinyl)hydroxymethyl]imidazo-[1,2-a]pyridine-3-carboxylate The title product is prepared from the title material of Example 89 by the method of Example 55.

EXAMPLE 94

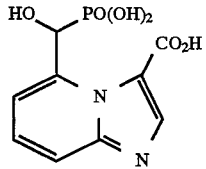

5-(hydroxyphosphonomethyl)imidazo[1,2-a]pyridine-3-carboxylic acid

The title material is prepared from the title product of Example 93 by the method of Example 7.

EXAMPLE 95

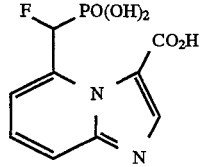

5-(fluorophosphonomethyl)imidazo[1,2-a]pyridine-3-carboxyilc acid

The title material is synthesized from the title product of Example 93 by the successive application of the methods of Examples 59 and 7.

BIOLOGICAL EVALUATION

NMDA-Selective Glutamate Binding Assay

Synaptic plasma membranes (SPM) were prepared as previously described [Monahan, J. B. and Michel, J., "Identification and Characterization of an N-methyl-D-aspartate-specific L[$^3$H]glutamate Recognition Site in Synaptic Plasma Membranes, *J. Neurochem.*, 48, 1699–1708 (1987)].

The SPM were stored at a concentration of 10–15 mg/ml in 0.32M sucrose, 0.5 mM EDTA, 1 mM MgSO$_4$, 5 mM Tris/SO$_4$, pH 7.4, under liquid nitrogen. The identity and purity of the subcellular fractions were confirmed by both electron microscopy and marker enzymes. Protein concentrations were determined by using a modification of the method of Lowry [Ohnishi, S. T. and Barr, J. K., "A Simplified Method of Quantitating Proteins using the Biuret and Phenol Reagents", *Anal. Biochem.*, 86, 193–197 (1978)]. The SPM were treated identically for the [$^3$H]AMPA (QUIS), [$^3$H]kainate and sodium-dependent L-[$^3$H]-glumatate binding assays. The SPM were thawed at room temperature, diluted twenty-fold with 50 mM Tris/acetate, pH 7.4, incubated at 37° C. for 30 minutes, and centrifuged at 100,000 g for 15 minutes. The dilution, incubation, and centrifugation was repeated a total of three times. Prior to use in the NMDA-specific L-[$^3$H]-glutamate binding assay the SPM were thawed, diluted twenty fold with 50 mM Tris/acetate, pH 7.4 containing 0.04% (v/v) Triton X-100, incubated for 30 minutes at 37° C. and centrifuged as described above. The Triton X-100 treated membranes were washed with 50 mM Tris/acetate, pH 7.4 and centrifuged at 100,000 g for 15 minutes a total of four times. Triton X-100 treatment of the SPM resulted in a higher affinity and more consistency in this L-[$^3$H]glutamate binding assay. For this reason the K$_d$ for glutamate and the K$_i$ values for other compounds are lower than previously reported; however, the pharmacological profile of this binding site was unaltered. The basic procedure for the receptor subclass binding assays was similar. this general method involved adding the radioligand (12.5 nM L-[$^3$H] glutamate; 0.5 nM [$^3$H]kainate or 10 nM [$^3$H]AMPA) to the appropriate concentration of the test compound and initiating the assay by the addition of ice cold synaptic plasma membranes (0.2–0.45 mg). The binding assays were performed in 1.5 mL centrifuge tubes with the total volume adjusted to 1.0 mL. Additions of test compounds were made in 50 mM Tris/acetate, pH 7.4 and incubations were carried out at 0°–4° C. The incubation time for the NMDA and the AMPA binding assays was 10 minutes, for the kainate binding assay 60 minutes and for the sodium-dependent glutamate binding assay 15 minutes. The AMPA binding assay contained 100 mM KSCN and the sodium-dependent glutamate binding assay contained 150 mM sodium acetate in addition to the previously described reagents. To terminate the incubation, the samples were centrifuged for 15 minutes at 12,000 g and 4° C. in a Beckman Microfuge 12. The supernatant was aspirated and the pelleted membranes dissolved in Beckman BTS-450 tissue solubilizer for a minimum of 6 hours at room temperature. Beckman MP scintillation cocktail containing 7 mL/l acetic acid was then added and the samples counted on a Beckman LS 5800 or 3801 liquid scintillation counter with automatic corrections for quenching and counting efficiency. Nonspecific binding was defined as the residual binding in the presence of either excess L-glutamate (0.1–0.4 mM), kainate (0.01 mM), or NMDA (0.5 mM), and was 15–25% of the total binding in the NMDA binding assay, 19–27% in the AMPA binding assay, 20–30% in the kainate binding assay and 10–15% in the sodium-dependent binding assay. Radioligand binding to the synaptic plasma membranes was analyzed using Scatchard and Hill transformations and the K$_i$ values of the compounds determined using logit-log transformations. Calculations and regression analysis were performed using templates developed for Lotus 1, 2, 3 as previously described [Pullan, L. M. "Automated Radioligand Receptor Binding Analysis with Templates for Lotus", *Computer Appln. Biosci.*, 3, 131 (1987)]. Binding results are reported in Table I for example compounds of the invention.

TABLE I

NMDA Receptor Binding Data

| Compound Ex. # | K$_i$ IC$_{50}$ Binding (μM) | | |
|---|---|---|---|
| | NMDA | KA | AMPA |
| 7 | 2.4 | 123 | >300 |
| 13 | >100 | >300 | >300 |
| 18 | >100 | >300 | >300 |
| 23 | 4.5 | >300 | >300 |
| 23* | 10.5 | | |
| 30 | >100 | >300 | >300 |
| 53 | >10 | | |
| 49 | >10 | | |
| 57 | 5.8 | 89 | >300 |
| 67 | >100 | >300 | >300 |

*Second batch

TCP Modulation Assay

The effect on the TCP (1-[1-(2-thienyl)-cyclohexyl] piperidine) binding was measured in rat brain synaptic membranes (SPM) prepared as previously described [J. B. Monahan & J. Michel; *J. Neurochem.* 48:1699–1708 (1987)]. Prior to their use in the binding assay, frozen SPM were thawed, diluted twenty fold with 50 mM Tris/acetate (pH 7.4 containing 0.04% (v/v) TritOn X-100), incubated for 30 min. at 37° C. and centrifuged at 95,000×g for 15 min. The Triton X-100 treated SPM were washed with 5 mM Tris/HCl, pH 7.4 and centrifuged a total of six times. The compound of Example #7 was incubated at different concentrations with SPM (0.2–0.4 mg protein) and 2 nM tritiated TCP, in a total volume of 0.5 ml of 5 mM Tris/HCl buffer pH 7.4 at 25° C. for 60 min. The samples were filtered through glass fiber filters (Schleicher & Schuell π32) which have been pretreated with 0.05% (v/v) polyethylenimine, washed 4 times with 2 ml of ice-cold 5 mM Tris/HCl buffer, and then counted on a Beckman LS 5800 liquid scintillation counter with automatic corrections for quenching and counting efficiency. Inhibition of TCP binding was measured as a decrease in the binding in the presence of 0.05 mM L-glutamate. Non-specific binding was defined as the residual binding in the presence of 60 mM phencyclidine. Results are shown in Table II.

TABLE II

TCP Binding Data

| Compound Ex. # | TCP K$_i$ IC$_{50}$ (μM) |
|---|---|
| 7 | 3.2 |
| 23 | 14.0 |
| 23* | 7.7 |
| 57 | (Antag.) |

*second batch

Forebrain Ischemia Assay

This assay was used to determine the extent of protection afforded by compound of the invention to neural brain cells subjected to ischemic conditions. Male Mongolian gerbils, 50–70 gm, were used as subjects. Compound No. 7 (30 mg/kg) was injected i.p. 30 minutes prior to carotid occlusion into 6 gerbils at two different doses (300 mg/kg and 500 mg/kg). In preparation for surgical procedures, the animals were lightly anesthetized with methoxyflurane and placed upside down on a heated pad with their snout within a nosecone. A 70:30 mixture of nitrous oxide and oxygen containing 0.5% halothane was circulated through the nosecone to provide continuous anesthesia throughout the surgical procedure. A midline incision was made in the neck and the carotid arteries were exposed. A length of suture thread was placed under each carotid. The thread was then tightened around each carotid and pressure applied to the thread to insure flow was occluded. Flow was occluded for 4–5 minutes and then the thread was removed. The carotids were visually inspected to confirm that reflow had occurred. The wound was then closed with autoclips and the gerbils allowed to recover. Following surgery, the gerbils were kept alive for 7 days. They were anesthetized with 100 mg/kg sodium pentobarbital and perfused transcardially with saline (with heparin) followed by buffered formalin. The brain was removed, trimmed and prepared for histological processing. Sections (10 microns) were stained with thionin. At 7 days following this type of transient global forebrain ischemia, damaged neurons in the vulnerable CA1 region of the hippocampus have degenerated and been cleared away by glia. Quantification of the resulting lesion is made by counting the pyramidal cell somata in a 0.5 mm length of CA1 of the hippocampus on the section corresponding to P 1.7 mm in the gerbil brain atlas.

Normal cell count in this region of the hippocampus in unoperated gerbils is 146±2. The effects of compound of Ex. #7 were assessed by comparing the number of neural cells found in the hippocampus of subjects treated with Ex. #7 compound with the cell number found in the appropriate control groups. The groups were compared by the Mann-Whitney U test [*Elementary Applied Statistics*, Wiley and Sons, New York (1965)]. The cell loss was significantly reduced in gerbils given compound of Ex. #7. Results are reported in Table III.

TABLE III

| Compound | Gerbil Ischemia Data | |
|---|---|---|
| | # of Neurons/Field | |
| Ex. #7 (500 mg/kg) | 112.6 | |
| CONTROL | 17.0 | P < 0.0001 |
| Ex. #7 (300 mg/kg) | 53.0 | |
| CONTROL) | 32.8 | P < 0.05 |

Anticonvulsant Assay

This assay was used to determine the extent of in vivo protection against convulsions afforded by compound of the invention to mice subjected to artifically-induced convulsive conditions. Naive male CD-1 mice (20–30 grams body weight) from Charles River Laboratories, Portage Mich. served as subjects. The mice had ad libitum access to food and water prior to testing and were maintained on a 12 hour light/12 hour dark schedule with testing during the light portion of the cycle. The mice were tested for motor impairment by use of the inverted screen test approximately 5 minutes prior to anticonvulsant testing. The inverted screen apparatus was similar to that described by Coughenour et al. [*Pharmacol. Biochem. Behav.* 6, 351–353 (1977)]. Mice were placed on 13×13 cm pieces of #4 wire mesh screen which were mounted horizontally. The screens were then slowly inverted. Mice that failed to climb to the tops of the inverted screens within 60 seconds were considered to have a motor impairment. Tonic hindlimb extensor seizures were then produced by application of electro-convulsive shock through concave electrodes to the eyeballs. Both the eyeballs and the electrodes were moistened with 0.9% saline to improve conductivity. The ECS stimulus was generated by use of a Grass model S48D stimulator with a Grass model CCU1A constant current unit in series with the output. Stimulation consisted of 10 msec pulses of a 60 pps single phase square wave for a duration of 200 msec. The current was held constant at 15 mA. Compound of Example #7 was suspended in a vehicle of 0.9% saline with a few drops of PG-Tween added. PG-Tween is a 1:1 mixture of propylene glycol and Tween 80. The Example #7 compound of vehicle was administered s.c. in a volume of 10 ml/kg body weight 30 minutes prior to application of the ECS stimulus. Immediately after ECS application, each mouse was observed for the presence or absence of a tonic himdlimb extensor seizure. There were 10 mice in each treatment group. The compound of Example #7 protected against tonic hindlimb extensor seizures in a dose-dependent fashion, and also impaired motor function in a similar dose range. Results are reported in Table IV below.

TABLE IV

| | Anticonvulsant Activity | |
|---|---|---|
| Dose Compound s.c. | Protected from ECS (% of Mice) | Exhibiting Motor Impairments (% of Mice) |
| 0(vehicle) | 5(n = 20) | 10(n = 20) |
| Example #7 - 10 mg/kg | 20 | 30 |
| Example #7 - 32 mg/kg | 60 | 50 |
| Example #7 - 56 mg/kg | 90 | 70 |
| Example #7 - 100 mg/kg | 100 | 90 |
| | $ED_{50} = 21.8$ (95% CI 12.3–32.9) | $ED_{50} = 24.6$ (95% CI 7–45.7) |

Assay for Effect on cGMP Levels in Cerebellum

The purpose of this assay is to determine the extent of in vivo bioavailability and the potency as an NMDA antagonist of compound of the invention as compared to known NMDA antagonists, namely, 3(2-carboxypiperizine-4-yl)propyl-1-phosphonic acid (CPP) and cis-4-phosphonomethyl-2-piperidinecarboxylic acid (CGS 19755). Male Swiss-Webster mice (17–24 g were injected sub-cutaneously (s.c.) with compound of the invention and the known NMDA antagonist standards 30 minutes prior to sacrifice by focussed microwave irradiation. Groups consisted of 7–10 mice. Compounds of Ex. #7 was dissolved in isotonic saline and all compounds were administered in a volume of 0.2 ml per mouse. Cerebella samples were extracted in IN HCl. Hydrochloric acid in extracts of the cerebellum were freeze-dried for assay of cGMP with a commercial RIA kit (NEN). Statistics (Dunett's t-test) were performed as described previously [P. L. Wood et al., *Neurochem.*, 19, 975–982 (1980)]. $ED_{50}$ values were calculated from log-logit transformation of the dose-response data. Results are reported in Table V.

TABLE V

| | Cerebellar cGMP Modulation |
|---|---|
| Compound | Decrease in cGMP $ED_{50}$ (mg/kg, s.c.) |
| Ex. #7 | 18.3 |
| CPP | 7.4 |
| CGS 19755 | 1.0 |

Compound of Ex. #7 was shown to be brain bioavailable by its ability to decrease levels of cGMP in mouse cerebellum. Also, compound of Ex. #7 was found to be in the same range of potency as the known NMDA antagonist CPP.

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a dispersion of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method to prevent excitatory amino acid induced neurotoxic injury in a subject, which method comprises administering to said subject a therapeutically effective amount of a compound of the formula:

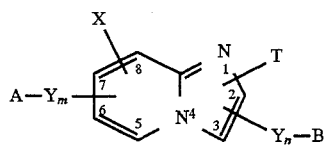

wherein each of A and B is an acidic moiety selected to contain at least one acidic hydrogen atom and wherein said acidic moiety is independently selected from carboxylic acid, phosphorus oxo acids, sulfur acids, thiophosphorus oxo acids and the amide, ester and salt derivatives of said acids;

wherein each of $Y_m$ and $Y_n$ is a group independently selected from one or more of alkyl, cycloalkyl, cycloalkylalkyl, alkenyl, alkynyl, sulfinyl, sulfonyl, aryl, and aralkyl, any one of which groups may be substituted at any substitutable position with one or more groups selected from alkyl, cycloalkyl, cycloalkylalkyl, oxo, halo, haloalkyl, alkenyl, cycloalkenyl, alkynyl, aryl, aralkyl, hydroxy, hydroxyalkyl, alkoxy, aryloxy, alkoxyalkyl, aralkoxy, aralkylthio, cyano, cyanoamino, nitro, alkanoyl, aroyl, mercapto, alkylthio, arylthio, alkylsulfinyl, arylsulfinyl, alkylsulfonyl, arylsulfonyl and amino and amido radicals of the formula

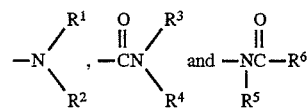

wherein each of $R^1$, $R^2$, $R^3$, $R^4$, $R^5$ and $R^6$ is independently selected from hydrido, alkyl, cycloalkyl, hydroxyalkyl, cycloalkylalkyl, alkoxyalkyl, aralkyl and aryl; wherein $R^1$ and $R^2$ taken together, $R^3$ and $R^4$ taken together and $R^5$ and $R^6$ taken together may form a heterocyclic group having five to seven ring members including the nitrogen atom of said amino or amido radical and which heterocyclic group may be saturated or partially unsaturated;

wherein $R^1$ and $R^2$ taken together and $R^3$ and $R^4$ taken together may form an aromatic heterocyclic group having five ring members including the nitrogen atom of said amino or amido radical; wherein each of m and n is a number independently selected from zero to five, inclusive;

wherein each x and T is one or more groups independently selected from hydrido, alkyl, cycloalkyl, cycloalkylalkyl, oxo, halo, haloalkyl, alkenyl, cycloalkenyl, alkynyl, aryl, aralkyl, hydroxy, hydroxyalkyl, alkoxy, aryloxy, alkoxyalkyl, aralkoxy, aralkylthio, cyano, cyanoamino, nitro, alkanoyl, mercapto, alkylthio, arylthio, alkylsulfinyl, arylsulfinyl, alkylsulfonyl, arylsulfonyl and amino and amido radicals of the formula

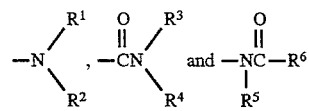

wherein each of $R^1$, $R^2$, $R^3$, $R^4$, $R^5$ and $R^6$ is independently selected from hydrido, alkyl, cycloalkyl, hydroxyalkyl, cycloalkylalkyl, alkoxyalkyl, aralkyl and aryl; and wherein $R^1$ and $R^2$ taken together, $R^3$ and $R^4$ taken together and $R^5$ and $R^6$ taken together may form a heterocyclic group having five to seven ring members including the nitrogen atom of said amino or amido radical and which heterocyclic group may be saturated or partially unsaturated; wherein $R^1$ and $R^2$ taken together and $R^3$ and $R^4$ taken together may form an aromatic heterocyclic group having five ring members including the nitrogen atom of said amino or amido radical;

provided A is a phosphorous oxo acid, and the amide, ester and salt derivatives thereof, when B is a carboxylic acid, and the alkyl ester and salt derivatives thereof;

or a pharmaceutically-acceptable salt thereof.

2. The method of claim 1 wherein each of A and B is an acidic moiety selected to contain at least one acidic hydrogen atom and wherein said acidic moiety is independently selected from carboxylic acid, sulfenic acid, sulfinic acid, sulfonic acid, and phosphorus oxo and thiophosphorus oxo acids selected from $$-\underset{R^7}{\overset{\overset{W}{\|}}{P}}-WH, \quad -\underset{R^8}{\overset{\overset{W}{\|}}{P}}-WH \quad \text{and} \quad -\underset{WR^9}{\overset{\overset{W}{\|}}{P}}-WH$$

wherein each W is independently selected from oxygen atom and sulfur atom; wherein each of $R^7$, $R^8$ and $R^9$ is independently selected from hydrido, alkyl, cycloalkyl, cycloalkylalkyl, aryl and aralkyl; wherein each of $R^7$ and $R^8$ may be further independently selected from amino radical of the formula $$-N\genfrac{}{}{0pt}{}{\diagup R^{10}}{\diagdown R^{11}}$$

wherein each of $R^{10}$ and $R^{11}$ is independently selected from hydrido, alkyl, cycloalkyl, hydroxyalkyl, haloalkyl, cycloalkylalkyl, alkoxyalkyl, aralkyl and aryl; wherein $R^{10}$ and $R^{11}$ taken together may form a heterocyclic group having five to seven ring members including the nitrogen atom of said amino radical and which heterocyclic group may be saturated or partially unsaturated;

wherein $R^{10}$ and $R^{11}$ taken together may form an aromatic heterocyclic group having five ring members including the nitrogen atom of said amino radical; wherein $R^7$ may be further independently selected from hydroxy, alkoxy, alkylthio, aryloxy, arylthio, aralkylthio and aralkoxy; and the amide, ester and salt derivatives of said acids; wherein each of $Y_m$ and $Y_n$ is a group independently selected from one or more of alkyl, alkenyl, alkynyl, aryl and aralkyl, any one of which groups may be substituted at any substitutable position with one or more groups selected from alkyl, cycloalkyl, cycloalkylalkyl, oxo, halo, haloalkyl, alkenyl, cycloalkenyl, alkynyl, aryl, aralkyl, hydroxy, hydroxyalkyl, alkoxy, aryloxy, alkoxyalkyl, aralkoxy, cyano, cyanoamino, nitro, alkanoyl, aroyl, mercapto, alkylthio, arylthio, alkylsulfinyl, alkylsulfonyl, arylsulfinyl, arylsulfonyl and amino and amido radicals of the formula

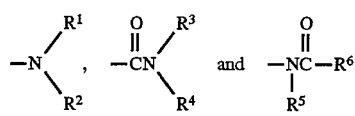

wherein each of $R^1$, $R^2$, $R^3$, $R^4$, $R^5$ and $R^6$ is independently selected from hydrido, alkyl, cycloalkyl, hydroxyalkyl, cycloalkylalkyl, alkoxyalkyl, phenalkyl and phenyl; and wherein $R^1$ and $R^2$ taken together, $R^3$ and $R^4$ taken together and $R^5$ and $R^6$ taken together may form a heterocyclic group having five to seven ring members including the nitrogen atom of said amino or amido radical and which heterocyclic group may be saturated or a partially unsaturated; wherein $R^1$ and $R^2$ taken together and $R^3$ and $R^4$ taken together may form an aromatic heterocyclic group having five ring members including the nitrogen atom of said amino or amido radical; wherein each of m and n is a number independently selected from zero to four, inclusive;

wherein each X and T is one or more groups independently selected from hydrido, alkyl, cycloalkyl, cycloalkylalkyl, halo, haloalkyl, alkenyl, cycloalkenyl, alkynyl, aryl, aralkyl, hydroxy, hydroxyalkyl, alkoxy, aryloxy, alkoxyalkyl, aralkoxy, cyano, cyanoamino, nitro, alkanoyl, mercapto, alkylthio, arylthio, alkylsulfinyl, alkylsulfonyl, arylsulfinyl, arylsulfonyl and amino and amido radicals of the formula

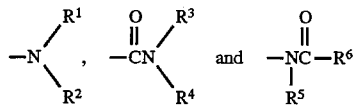

wherein each of $R^1$, $R^2$, $R^3$, $R^4$, $R^5$ and $R^6$ is independently selected from hydrido, alkyl, cycloalkyl, hydroxyalkyl, cycloalkylalkyl, alkoxyalkyl, phenalkyl and phenyl; and wherein $R^1$ and $R^2$ taken together, $R^3$ and $R^4$ taken together and $R^5$ and $R^6$ taken together may form a heterocyclic group having five to seven ring members including the nitrogen atom of said amino or amido radical and which heterocyclic group may be saturated or partially unsaturated; wherein $R^1$ and $R^2$ taken together and $R^3$ and $R^4$ taken together may form an aromatic heterocyclic group having five ring members including the nitrogen atom of said amino or amido radical; or a pharmaceutically-acceptable acid addition salt thereof.

3. The method of claim 2 wherein each of A and B is an acidic moiety selected to contain at least one acidic hydrogen atom and wherein said acidic moiety is independently selected from carboxylic acid and sulfonic acid, and selected from phosphinous acids, phosphonous acids and phosphonic acids of the formula $$-\underset{R^7}{\overset{\overset{O}{\|}}{P}}OH, \quad -\underset{R^8}{\overset{\overset{O}{\|}}{P}}OH, \quad -\underset{OR^9}{\overset{\overset{O}{\|}}{P}}OH,$$

wherein each of $R^7$, $R^8$ and $R^9$ is independently selected from hydrido, alkyl, cycloalkyl, cycloalkylalkyl, phenyl, phenalkyl, and wherein each of $R^7$ and $R^8$ may be further independently selected from amino radical of the formula

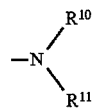

wherein each of R¹⁰ and R¹¹ is independently selected from hydrido, alkyl, cycloalkyl, hydroxyalkyl, haloalkyl, cycloalkylalkyl, alkoxyalkyl, aralkyl and aryl; wherein R¹⁰ and R¹¹ taken together may form a heterocyclic group having five to seven ring members including the nitrogen atom of said amino radical and which heterocyclic group may be saturated or partially unsaturated; wherein R¹⁰ and R¹¹ taken together may form an aromatic heterocyclic group having five ring members including the nitrogen atom of said amino radical; wherein R⁷ is further selected from hydroxy, alkoxy, phenoxy, benzyloxy, benzylthio, mercapto, alkylthio and phenylthio; and the monoalkylamide, dialkylamide, alkylester and salt derivatives of said acids;

wherein each of $Y_m$ and $Y_n$ is a group independently selected from one or more of alkyl, alkenyl, alkynyl, aryl and aralkyl, any one of which groups may be substituted at any substitutable position with one or more groups selected from alkyl, cycloalkyl, cycloalkylalkyl, oxo, halo, haloalkyl, alkenyl, cycloalkenyl, alkynyl, phenyl, benzyl, hydroxy, hydroxyalkyl, alkoxy, phenoxy, alkoxyalkyl, benzyloxy, cyano, cyanoamino, nitro, alkanoyl, benzoyl, mercapto, alkylthio, arylthio, alkylsulfinyl, alkylsulfonyl, arylsulfinyl, arylsulfonyl and amino and amido radicals of the formula

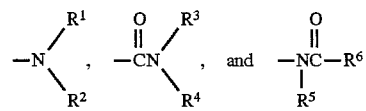

wherein each of R¹, R², R³, R⁴, R⁵ and R⁶ is independently selected from hydrido, alkyl, cycloalkyl, hydroxyalkyl, alkoxyalkyl, benzyl and phenyl; and wherein R₁ and R² taken together, R³ and R⁴ taken together and R⁵ and R⁶ taken together may for a heterocyclic group having five ring members including the nitrogen atom of said amino or amido radical and which heterocyclic group may be saturated or partially unsaturated; wherein R¹ and R² taken together and R³ and R⁴ taken together may form an aromatic heterocyclic group having five to seven ring members including the nitrogen atom of said amino or amido radical; wherein each of m and n is a number independently selected from zero to three, inclusive;

wherein each X and T is one or more groups independently selected from hydrido, alkyl, cycloalkyl, cycloalkylakyl, halo, haloalkyl, alkenyl, cycloalkenyl, alkynyl, phenyl, benzyl, hydroxy, hydroxyalkyl, alkoxy, phenoxy, alkoxyalkyl, benzyloxy, cyano, cyanoamino, nitro, alkanoyl, mercapto, alkylthio, arylthio, alkylsulfinyl, alkylsulfonyl, arylsulfinyl, arylsulfonyl and amino and amido radicals of the formula

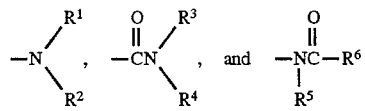

wherein each of R¹, R², R³, R⁴, R⁵ and R⁶ is independently selected from hydrido, alkyl, cycloalkyl, hydroxyalkyl, alkoxyalkyl, benzyl and phenyl; and wherein R¹ and R² taken together, R³ and R⁴ taken together and R⁵ and R⁶ taken together may form a heterocyclic group having five to seven ring members including the nitrogen atom of said amino or amido radical and which heterocyclic group may be saturated or partially unsaturated; wherein R¹ and R² taken together and R³ and R⁴ taken together may form an aromatic heterocyclic group having five ring members including the nitrogen atom of said amino or amido radical; or a pharmaceutically-acceptable acid addition salt thereof.

4. The method of claim 3 wherein each of A and B is an acidic moiety selected to contain at least one acidic hydrogen atom and wherein said acidic moiety is independently selected from carboxylic acid, and selected from phosphonous acids and phosphonic acids of the formula

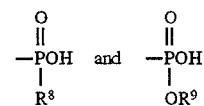

wherein each of R⁸ and R⁹ is independently selected from hydrido, alkyl, cycloalkyl, cycloalkylalkyl, phenyl and benzyl; and wherein R⁸ is further selected from amino radical of the formula

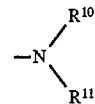

wherein each of R¹⁰ and R¹¹ is independently selected from hydrido, alkyl, cycloalkyl, cycloalkylalkyl, phenyl and benzyl; and wherein R¹⁰ and R¹¹ taken together may form a heterocyclic group having five to seven ring members including the nitrogen atom of said amino radical and which heterocyclic group may be saturated or partially unsaturated; wherein R¹⁰ and R¹¹ taken together and R³ and R⁴ taken together may form an aromatic heterocyclic group having five ring members including the nitrogen atom of said amino radical; and the monoalkylamide, dialkylamide, alkylester and salt derivatives of said acids;

wherein each of $Y_m$ and $Y_n$ is a group independently selected from one or more of alkyl, alkenyl, alkynyl, aryl and aralkyl, any one of which groups may be substituted at any substitutable position with one or more groups selected from alkyl, cycloalkyl, oxo, halo, haloalkyl, phenyl, benzyl, hydroxy, hydroxyalkyl, alkoxy, phenoxy, alkoxyalkyl, benzyloxy, cyano, alkanoyl and amino and amido radicals of the formula

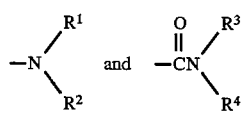

wherein each of $R^1$, $R^2$, $R^3$ and $R^4$ is independently selected from hydrido, alkyl, phenyl and benzyl; wherein each of m and n is a number independently selected from zero to three, inclusive;

wherein each X and T is one or more groups independently selected from hydrido, alkyl, cycloalkyl, cycloalkylalkyl, halo, haloalkyl, alkenyl, cycloalkenyl, alkynyl, phenyl, benzyl, hydroxy, hydroxyalkyl, alkoxy, alkoxyalkyl, benzyloxy, cyano, cyanoamino, alkanoyl, mercapto, alkylthio, arylthio, alkylsulfinyl, alkylsulfonyl, arylsulfinyl, arylsulfonyl, and amino and amido radicals of the formula

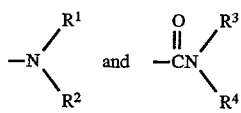

wherein each of $R^1$, $R^2$, $R^3$ and $R^4$ is independently selected from hydrido, alkyl, phenyl and benzyl; or a pharmaceutically-acceptable acid addition salt thereof.

5. The method of claim 4 wherein A is selected from phosphonic acids of the formula

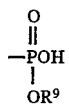

wherein $R^9$ is selected from hydrido, alkyl, cycloalkyl, phenyl and benzyl; wherein A is further selected from the full alkyl esters and metal salts of the phosphonic acids of said formula; wherein B is independently selected from carboxylic acid and alkyl ester and salts thereof;

wherein each of $Y_m$ and $Y_n$ is a group independently selected from one or more groups of the formula

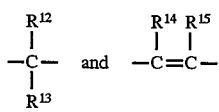

wherein each of $R^{12}$ and $R^{13}$ is independently selected from hydrido, alkyl, cycloalkyl, halo, haloalkyl, phenyl, benzyl, hydroxy, hydroxyalkyl, alkoxy, phenoxy, alkoxyalkyl, benzyloxy, cyano, alkanoyl,

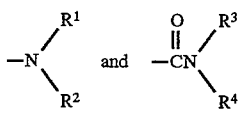

wherein each of $R^1$, $R^2$, $R^3$ and $R^4$ is independently selected from hydrido, alkyl and phenyl; wherein $R^{12}$ and $R^{13}$ may be taken together to form oxo; wherein each of $R^{14}$ and $R^{15}$ is independently selected from hydrido, alkyl, haloalkyl, phenyl, hydroxyalkyl and alkoxyalkyl; wherein each of m and n is a number independently selected from zero to three, inclusive;

wherein each X and T is one or more groups independently selected from hydrido, alkyl, cycloalkyl, cycloalkylalkyl, halo, haloalkyl, alkenyl, cycloalkenyl, alkynyl, phenyl, benzyl, hydroxy, hydroxyalkyl, alkoxy, phenoxy, alkoxyalkyl, benzyloxy, cyano, cyanoamino, alkanoyl, mercapto, alkylthio, arylthio, alkylsulfinyl, alkylsulfonyl, arylsulfinyl and arylsulfonyl,

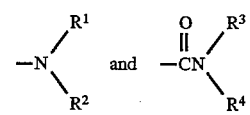

wherein each of $R^1$, $R^2$, $R^3$ and $R^4$ is independently selected from hydrido, alkyl and phenyl; or a pharmaceutically-acceptable acid addition salt thereof.

6. The method of claim 5 wherein A is selected from phosphonic acids of the formula

wherein $R^9$ is selected from hydrido, methyl, ethyl, n-propyl, isopropyl, n-butyl, isobutyl, sec-butyl, tert-butyl, cyclopropyl, cyclobutyl, cyclopentyl, cyclohexyl and cycloheptyl; wherein A is further selected from the full alkyl esters and salts of the phosphonic acids of said formula; wherein B is independently selected from carboxylic acid and alkyl esters and salts thereof;

wherein each of $Y_m$ and $Y_n$ is a group independently selected from one or more groups of the formula

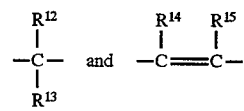

wherein each of $R^{12}$ and $R^{13}$ is independently selected from hydrido, alkyl, cycloalkyl, halo, haloalkyl, hydroxy, hydroxyalkyl, alkoxy, alkoxyalkyl, alkanoyl,

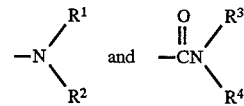

wherein each of $R^1$, $R^2$, $R^3$ and $R^4$ is independently selected from hydrido and alkyl; wherein $R^{12}$ and $R^{13}$ may be taken together to form oxo; wherein each of $R^{14}$ and $R^{15}$ is independently selected from hydrido, alkyl, haloalkyl, hydroxyalkyl and alkoxyalkyl; wherein each of m and n is a number independently selected from zero to three, inclusive.

wherein each X and T is one or more groups independently selected from hydrido, alkyl, cycloalkyl, halo, haloalkyl, phenyl, benzyl, hydroxy, hydroxyalkyl, alkoxy, phenoxy, alkoxyalkyl, benzyloxy, alkanoyl,

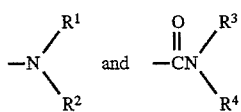

wherein each of $R^1$, $R^2$, $R^3$ and $R^4$ is independently selected from hydrido and alkyl; or a pharmaceutically-acceptable acid addition salt thereof.

7. The method of claim 6 wherein said compound is of the formula

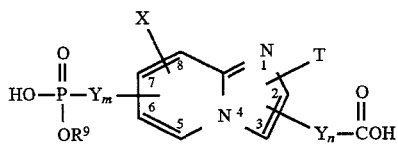

and the carboxylic and phosphonic alkyl esters and salts thereof; wherein $R^9$ is selected from hydrido, methyl, ethyl, n-propyl, isopropyl, n-butyl, isobutyl, sec-butyl, tert-butyl, cyclopropyl, cyclobutyl, cyclopentyl, cyclohexyl and cycloheptyl;

wherein each of $Y_m$ and $Y_n$ is a group independently selected from one or more methylene or ethylene radicals of the formula

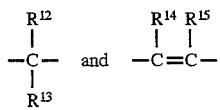

wherein each of $R^{12}$ and $R^{13}$ is independently selected from hydrido, alkyl, halo, haloalkyl, hydroxy, hydroxyalkyl, alkoxy, alkoxyalkyl and alkanoyl; wherein $R^{12}$ and $R^{13}$ may be taken together to form oxo; wherein each of $R^{14}$ and $R^{15}$ is independently selected from hydrido, alkyl, haloalkyl, hydroxyalkyl and alkoxyalkyl; wherein each of m and n is a number independently selected from zero to two, inclusive;

wherein each X and T is one or more groups independently selected from hydrido, alkyl, cycloalkyl, halo, haloalkyl, hydroxy, hydroxyalkyl, alkoxy, alkoxyalkyl and alkanoyl; or a pharmaceutically-acceptable acid addition salt thereof.

8. The method of claim 7 wherein said compound is selected from the group consisting of
ethyl 5-[(diethoxyphosphinyl)methyl]imidazo[1,2-a]pyridine-2-carboxylate;
5-(phosphonomethyl)imidazo[1,2-a]pyridine-2-carboxylic acid;
ethyl 6-[(diethoxyphosphinyl)methyl]imidazo[1,2-a]pyridine-2-carboxylate;
6-(phosphonomethyl)imidazo[1,2-a]pyridine-2-carboxylic acid;
ethyl 7-[(diethoxyphosphinyl)methyl]imidazo[1,2-a]pyridine-2-carboxylate;
7-(phosphonomethyl)imidazo[1,2-a]pyridine-2-carboxylic acid;
ethyl 8-[(diethoxyphosphinyl)methyl]imidazo[1,2-a]pyridine-2-carboxylate;
8-(phosphonomethyl)imidazo[1,2-a]pyridine-2-carboxylic acid;
ethyl 6-chloro-5-[(diethoxyphosphinyl)methyl]imidazo[1,2-a]pyridine-2-carboxylate;
6-chloro-5-(phosphonomethyl)imidazo[1,2-a]pyridine2-carboxylic acid;
ethyl 7-chloro-5-[(diethoxyphosphinyl)methyl]imidazo[1,2-a]pyridine-2-carboxylate;
7-chloro-5-(phosphonomethyl)imidazo[1,2-a]pyridine-2carboxylic acid;
ethyl 5-[(diethoxyphosphinyl)methyl]-7-methoxyimidazo[1,2-a]pyridine-2-carboxylate;
7-methoxy-5-(phosphonomethyl)imidazo[1,2-a]pyridine-2carboxylic acid;
ethyl 8-(diethoxyphosphinyl)-5-methylimidazo[1,2-a]pyridine-2-carboxylate;
5-methyl-8-phosphonoimidazo[1,2-a]pyridine-2-carboxylic acid;
ethyl 5-(diethoxyphosphinyl)imidazo[1,2-a]pyridine-2carboxylate;
ethyl 5-(diethoxyphosphinyl)imidazo[1,2-a]pyridine2-carboxylate, monohydrochloride;
5-phosphonoimidazo[1,2-a]pyridine-2-carboxylic acid;
ethyl 5-[(diethoxyphosphinyl)hydroxymethyl]imidazo[1,2-a]pyridine-2-carboxylate;
ethyl 5-[(diethoxyphosphinyl)hydroxymethyl]imidazo[1,2-a]pyridine-2-carboxylate, monohydrochloride;
5-(hydroxyphosphonomethyl)imidazo[1,2-a]pyridine-2carboxylic acid, monohydrochloride;
ethyl 5-[2-(diethoxyphosphinyl)-E-ethenyl]imidazo[1,2-a]pyridine-2-carboxylate;
5-(2-phosphono-E-ethenyl)imidazo[1,2-a]pyridine-2carboxylic acid;
5-(2-phosphonoethyl)imidazo[1,2-a]pyridine-2-carboxylic acid;
ethyl 8-[(diethoxyphosphinyl)methyl]-3-methylimidazo[1,2-a]pyridine-2-carboxylate;
ethyl 8-[(diethoxyphosphinyl)methyl]-3-methylimidazo[1,2-a]pyridine-2-carboxylate;
3-methyl-8-(phosphonomethyl)imidazo[1,2-a]pyridine-2carboxylic acid, monohydrochloride;
ethyl 5-[(diethoxyphosphinyl)methyl]imidazo[1,2-a]pyridine-3-carboxylate;
5-(phosphonomethyl)imidazo[1,2-a]pyridine-3-carboxylic acid;
6-(phosphonomethyl)imidazo[1,2-a]pyridine-3-carboxylic acid;
8-(phosphonomethyl)imidazo[1,2-a]pyridine-3-carboxylic acid;
ethyl 7-[(diethoxyphosphinyl)methyl]imidazo[1,2-a]pyridine-3-carboxylate;
7-(phosphonomethyl)imidazo[1,2-a]pyridine-3-carboxylic acid;
ethyl 6-chloro-5-[(diethoxyphosphinyl)methyl]imidazo[1,2-a]pyridine-3-carboxylate;
6-chloro-5-(phosphonomethyl)imidazo[1,2-a]pyridine-3carboxylic acid;
ethyl 5-[(diethoxyphosphinyl)methyl]-7-methoxyimidazo[1,2-a]pyridine-3-carboxylate;
7-methoxy-5-(phosphonomethyl)imidazo[1,2-a]pyridine-3carboxylic acid;
ethyl 7-chloro-5-[(diethoxyphosphinyl)methyl]imidazo[1,2-a]pyridine-3-carboxylate;
7-chloro-5-(phosphonomethyl)imidazo[1,2-a]pyridine-3carboxylic acid;
ethyl 8-(diethoxyphosphinyl)-5-methylimidazo[1,2-a]pyridine-3-carboxylate;
5-methyl-8-phosphonoimidazo[1,2-a]pyridine-3-carboxylic acid;
ethyl 5-(diethoxyphosphinyl)imidazo[1,2-a]pyridine-3carboxylate;
5-phosphonoimidazo[1,2-a]pyridine-3-carboxylic acid;

ethyl 5-[2-(diethoxyphosphinyl)-E-ethenyl]imidazo[1,2-a]pyridine-3-carboxylate;

5-(2-phosphono-E-ethenyl)imidazo[1,2-a]pyridine-3carboxylic acid;

5-(2-phosphonoethyl)imidazo[1,2-a]pyridine-3-carboxylic acid;

ethyl 5-[(diethoxyphosphinyl)hydroxymethyl]imidazo[1,2-a]pyridine-3-carboxylate;

5-(hydroxyphosphonomethyl)imidazo[1,2-a]pyridine-3carboxylic acid;

5-(fluorophosphonomethyl)imidazo[1,2-a]pyridine-3carboxylic acid;

the alkyl esters and salts of the phosphonic acid groups and carboxylic acid groups of said compounds; or a pharmaceutically-acceptable acid addition salt thereof.

9. The method of claim 8 wherein said compound selected from the group consisting of ethyl 5-[(diethoxyphosphinyl)methyl]imidazo[1,2-a]pyridine-2-carboxylate;

5-(phosphonomethyl)imidazo[1,2-a]pyridine-2-carboxylic acid;

6-(phosphonomethyl)imidazo[1,2-a]pyridine-2-carboxylic acid;

ethyl 7-[(diethoxyphosphinyl)methyl]imidazo[1,2-a]pyridine-2-carboxylate;

7-(phosphonomethyl)imidazo[1,2-a]pyridine-2-carboxylic acid;

8-(phosphonomethyl)imidazo[1,2-a]pyridine-2-carboxylic acid;

ethyl 6-chloro-5-[(diethoxyphosphinyl)methyl]imidazo[1,2-a]pyridine-2-carboxylate;

6-chloro-5-(phosphonomethyl)imidazo[1,2-a]pyridine2-carboxylic acid;

5-methyl-8-phosphonoimidazo[1,2-a]pyridine-2-carboxylic acid;

5-phosphonoimidazo[1,2-a]pyridine-2-carboxylic acid;

ethyl 5-[(diethoxyphosphinyl)hydroxymethyl]imidazo[1,2-a]pyridine-2-carboxylate, monohydrochloride;

5-(hydroxyphosphonomethyl)imidazo[1,2-a]pyridine-2carboxylic acid, monohydrochloride;

ethyl 8-[(diethoxyphosphinyl)methyl]-3-methylimidazo[1,2-a]pyridine-2-carboxylate;

3-methyl-8-(phosphonomethyl)imidazo[1,2-a]pyridine-2carboxylic acid, monohydrochloride;

the alkyl esters and salts of the phosphonic acid and carboxylic acid groups of said compounds; or a pharmaceutically-acceptable acid addition salt thereof.

10. The method of claim 9 wherein said compound is ethyl 5-[(diethoxyphosphinyl)methyl]imidazo[1,2-a]pyridine-2-carboxylate; or a pharmaceutically-acceptable acid addition salt thereof.

11. The method of claim 9 wherein said compound is 5-(phosphonomethyl)imidazo[1,2-a]pyridine2-carboxylic acid; or a pharmaceutically-acceptable acid addition salt thereof.

12. The method of claim 9 wherein said compound is 6-(phosphonomethyl)imidazo[1,2-a]pyridine2-carboxylic acid; or a pharmaceutically-acceptable acid addition salt thereof.

13. The method of claim 9 wherein said compound is ethyl 7-[(diethoxyphosphinyl)methyl]imidazo[1,2-a]pyridine-2-carboxylate; or a pharmaceutically-acceptable acid addition salt thereof.

14. The method of claim 9 wherein said compound is 7-(phosphonomethyl)imidazo[1,2-a]pyridine2-carboxylic acid; or a pharmaceutically-acceptable acid addition salt thereof.

15. The method of claim 9 wherein said compound is 8-(phosphonomethyl)imidazo[1,2-a]pyridine2-carboxylic acid; or a pharmaceutically-acceptable acid addition salt thereof.

16. The method of claim 9 wherein said compound is ethyl 6-chloro-5-[(diethoxyphosphinyl)methyl]imidazo[1,2-a]pyridine-2-carboxylate; or a pharmaceutically-acceptable acid addition salt thereof.

17. The method of claim 9 wherein said compound is 6-chloro-5-(phosphonomethyl)imidazo[1,2a]pyridine-2-carboxylic acid; or a pharmaceutically-acceptable acid addition salt thereof.

18. The method of claim 9 is wherein said compound 5-methyl-8-phosphonoimidazo[1,2-a]pyridine-2-carboxylic acid; or a pharmaceutically-acceptable acid addition salt thereof.

19. The method of claim 9 wherein said compound is 5-phosphonoimidazo[1,2-a]pyridine-2-carboxylic acid; or a pharmaceutically-acceptable acid addition salt thereof.

20. The method of claim 9 wherein said compound is ethyl 5-[(diethoxyphosphinyl)hydroxymethyl]imidazo-[1,2-a]pyridine-2-carboxylate, monohydrochloride; or a pharmaceutically-acceptable acid addition salt thereof.

21. The method of claim 9 wherein said compound is 5-(hydroxyphosphonomethyl)imidazo[1,2a]pyridine-2-carboxylic acid, monohydrochloride; or a pharmaceutically-acceptable acid addition salt thereof.

22. The method of claim 9 wherein said compound is ethyl 8-[(diethoxyphosphinyl)methyl]-3-methylimidazo[1,2-a]pyridine-2-carboxylate; or a pharmaceutically-acceptable acid addition salt thereof.

23. The method of claim 9 wherein said compound is 3-methyl-8-(phosphonomethyl)imidazo[1,2a]pyridine-2-carboxylic acid, monohydrochloride; or a pharmaceutically-acceptable acid addition salt thereof.

* * * * *